US012754481B2

(12) United States Patent
Lim

(10) Patent No.: US 12,754,481 B2
(45) **Date of Patent: *Oct. 6, 2026**

(54) HARDMASK COMPOSITION, HARDMASK LAYER, AND PATTERN FORMING METHOD

(71) Applicant: SAMSUNG SDI CO., LTD., Yongin-si (KR)

(72) Inventor: Jaebum Lim, Yongin-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 899 days.

This patent is subject to a terminal disclaimer.

(21) Appl. No.: 17/642,734

(22) PCT Filed: Jun. 3, 2020

(86) PCT No.: PCT/KR2020/007214

§ 371 (c)(1),
(2) Date: Mar. 14, 2022

(87) PCT Pub. No.: WO2021/054570

PCT Pub. Date: Mar. 25, 2021

(65) Prior Publication Data

US 2022/0334489 A1 Oct. 20, 2022

(30) Foreign Application Priority Data

Sep. 17, 2019 (KR) ........................ 10-2019-0114297

(51) Int. Cl.

*G03F 7/20* (2006.01)
*C07C 43/285* (2006.01)
*C07D 403/10* (2006.01)
*G03F 7/004* (2006.01)
*G03F 7/11* (2006.01)

(52) U.S. Cl.

CPC .......... *G03F 7/2016* (2013.01); *C07C 43/285* (2013.01); *C07D 403/10* (2013.01); *G03F 7/0041* (2013.01); *G03F 7/11* (2013.01)

(58) Field of Classification Search

None
See application file for complete search history.

(56) References Cited

U.S. PATENT DOCUMENTS 5,965,679 A * 10/1999 Godschalx ............. C08G 61/10 526/281
5,968,679 A 10/1999 Kobayashi et al.
9,534,097 B2 1/2017 Hibbs et al.
11,409,197 B2 * 8/2022 Lim .......................... G03F 7/11
2003/0039858 A1 2/2003 Igarashi et al.
2003/0099838 A1 * 5/2003 Cho ....................... C08G 73/10 528/401
2004/0232409 A1 * 11/2004 Igarashi ............... H10K 85/624 257/40
2005/0124172 A1 6/2005 Townsend, III et al.
2010/0021830 A1 1/2010 Kim et al.
2012/0153511 A1 * 6/2012 Song ................. H01L 21/31144 257/E23.06
2013/0280655 A1 10/2013 Higashihara et al.
2015/0059854 A1 3/2015 Shiba et al.
2015/0166711 A1 6/2015 Cui et al.
2015/0267046 A1 9/2015 Namai et al.
2016/0017174 A1 1/2016 Nam et al.
2016/0060393 A1 * 3/2016 Gilmore .............. H01L 23/5329 524/111
2016/0085152 A1 3/2016 Nakafuji et al.
2016/0291472 A1 10/2016 Shin et al.
2017/0227850 A1 8/2017 Nishimaki et al.
2018/0157175 A1 6/2018 Liu et al.
2018/0158674 A1 6/2018 Yamada et al.
2019/0163063 A1 * 5/2019 Sakaida ........... C08G 65/33396
2020/0044158 A1 * 2/2020 Nakasugi ................ C07C 39/15
2020/0201185 A1 6/2020 Lim et al.

FOREIGN PATENT DOCUMENTS

CN 1867646 A * 11/2006
CN 102566281 A 7/2012
CN 108148180 A 6/2018
CN 110088072 A 8/2019
JP 2002324678 A * 11/2002
JP 2004-356582 A 12/2004
JP 3760221 B2 * 3/2006
JP 2007015993 A * 1/2007 ........... H10K 85/654
JP 4003824 B2 11/2007
JP 4531400 B2 8/2010
JP 2012046428 A * 3/2012
JP 6130757 B2 5/2017
(Continued)

OTHER PUBLICATIONS

Shifrina et al, 2005 Poly(phenylene-pyridyl) dendrimers: synthesis and templating of metal nanoparticles, Macromolecules 2005, 38, 9920-9932 (Year: 2005).*
(Continued)

*Primary Examiner* — Martin J Angebranndt
(74) *Attorney, Agent, or Firm* — Lee IP Law, P.C.

(57) ABSTRACT

The present invention relates to a hardmask composition including a compound represented by Chemical Formula 1 and a solvent, a hardmask layer including a cured product of the hardmask composition, and a pattern forming method using the hardmask composition.

[Chemical Formula 1]

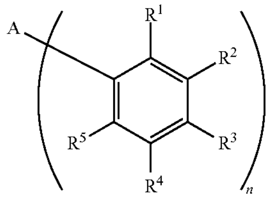

In Chemical Formula 1, the definitions of A, $R^1$ to $R^5$, and n are as described in the specification.

16 Claims, No Drawings

(56) References Cited

FOREIGN PATENT DOCUMENTS

| | | | | | |
|---|---|---|---|---|---|
| JP | 2017155003 | A | * | 9/2017 | |
| KR | 10-0866015 | B1 | | 10/2008 | |
| KR | 10-1225945 | B1 | | 1/2013 | |
| KR | 10-1225946 | B1 | | 1/2013 | |
| KR | 10-1344793 | B1 | | 12/2013 | |
| KR | 10-2015-0110354 | A | | 10/2015 | |
| KR | 10-2016-0023696 | A | | 3/2016 | |
| KR | 10-2016-0118782 | A | | 10/2016 | |
| KR | 10-2017-0042500 | A | | 4/2017 | |
| KR | 10-1747229 | B1 | | 6/2017 | |
| KR | 10-1775898 | B1 | | 9/2017 | |
| KR | 10-2018-0064286 | A | | 6/2018 | |
| KR | 10-2019-0081972 | A | | 7/2019 | |
| KR | 10-2019-0100280 | A | | 8/2019 | |
| WO | WO-2018115043 | A1 | * | 6/2018 | ............. C07C 39/04 |

OTHER PUBLICATIONS

Hashim et al. "Dissecting porosity in Molecular Crystals: Influence of Geometry, Hydrogen Bonding, and [π···π] Stacking on the Solid-State Packing of Fluorinated Aromatics", JACS, vol. 140 pp. 6014-6026 (2018).*

International Search Report dated Sep. 15, 2020 for PCT/KR2020/007214.

Chinese Office action dated Mar. 26, 2025.

* cited by examiner

HARDMASK COMPOSITION, HARDMASK LAYER, AND PATTERN FORMING METHOD

CROSS REFERENCE TO RELATED APPLICATIONS

This is the U.S. national phase application based on PCT Application No. PCT/KR2020/007214, filed Jun. 3, 2020, which is based on Korean Patent Application No. 10-2019-0114297, filed Sep. 17, 2019, the entire contents of all of which are hereby incorporated by reference.

BACKGROUND OF THE INVENTION

(a) Field of the Invention

A hardmask composition, a hardmask layer including a cured product of the hardmask composition, and a pattern forming method using the hardmask composition are disclosed.

(b) Description of the Related Art

Recently, the semiconductor industry has developed to an ultra-fine technique having a pattern of several to several tens of nanometer size. Such ultrafine technique essentially needs effective lithographic techniques. A typical lithographic technique includes providing a material layer on a semiconductor substrate; coating a photoresist layer thereon; exposing and developing the same to provide a photoresist pattern; and etching a material layer using the photoresist pattern as a mask. Nowadays, according to small-sizing the pattern to be formed, it is difficult to provide a fine pattern having an excellent profile by only above-mentioned typical lithographic technique. Accordingly, an auxiliary layer, called a hardmask layer, may be formed between the material layer and the photoresist layer to provide a fine pattern.

SUMMARY OF THE INVENTION

Technical Problem

An embodiment provides a hardmask composition capable of improving etch resistance.

Another embodiment provides a hardmask layer including a cured product of the hardmask composition.

Another embodiment provides a pattern forming method using the hardmask composition.

Technical Solution

According to an embodiment, provided is a hardmask composition including a compound represented by Chemical Formula 1 and a solvent.

[Chemical Formula 1]

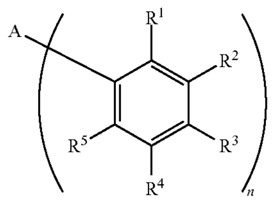

In Chemical Formula 1,

A is a C6 to C30 aromatic moiety, $R^1$ to $R^5$ are each independently hydrogen, a substituted or unsubstituted C6 to C30 aryl group, a substituted or unsubstituted C3 to C30 heteroaryl group, or a combination thereof or a group represented by Chemical Formula 2, at least one of $R^1$ to $R^5$ is a group represented by a group represented by Chemical Formula 2, and n is an integer greater than or equal to 2,

[Chemical Formula 2]

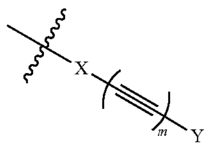

wherein, in Chemical Formula 2,

X is a substituted or unsubstituted C6 to C30 arylene group,

Y is a substituted C6 to C60 aryl group or a substituted or unsubstituted C3 to C60 heteroaryl group, wherein the substituted C6 to C60 aryl group includes a substitutent selected from hydroxy group, amine group, mercapto group, a substituted or unsubstituted C1 to C30 alkoxy group, a substituted or unsubstituted C1 to C30 alkylthiol group, a substituted or unsubstituted C1 to C20 alkylamine group, a substituted or unsubstituted C3 to C30 heteroaryl group, or a combination thereof, m is 0 or 1, and

, indicates a linking point with Chemical Formula 1.

A may be a benzene moiety, a naphthalene moiety, an anthracene moiety, a tetracene moiety, a pentacene moiety, a biphenyl moiety, a terphenyl moiety, a quaterphenyl moiety, or a quinquephenyl moiety, a phenanthrene moiety, a pyrene moiety, a fluoranthene moiety, a benzophenanthrene moiety, a chrysene moiety, a perylene moiety, a benzopyrene moiety, a picene moiety, a benzofluoranthene moiety, a dibenzofluoranthene moiety, a benzoperylene moiety, a coronene moiety, a naphthoanthracene moiety, or a triphenylene moiety.

A may be any one selected from Group 1.

[Group 1]

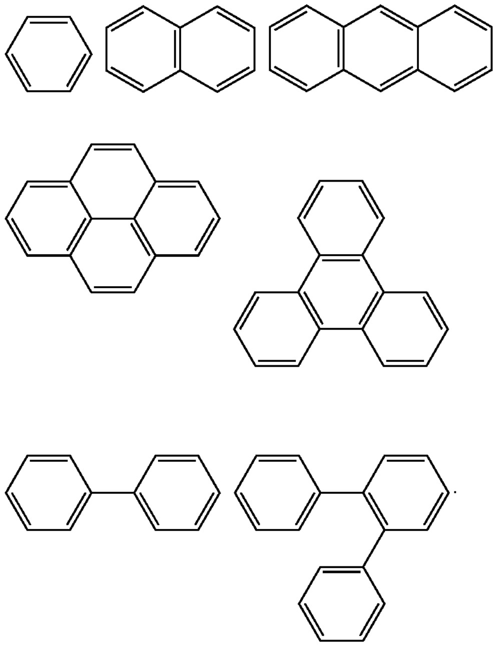

$R^1$, $R^2$, $R^4$, and $R^5$ may each independently be hydrogen or a substituted or unsubstituted group selected from Group 2, and $R^3$ may be the group represented by Chemical Formula 2.

[Group 2]

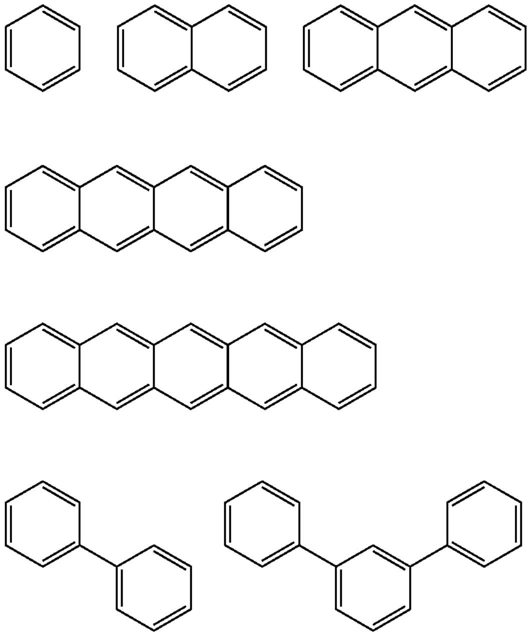

-continued

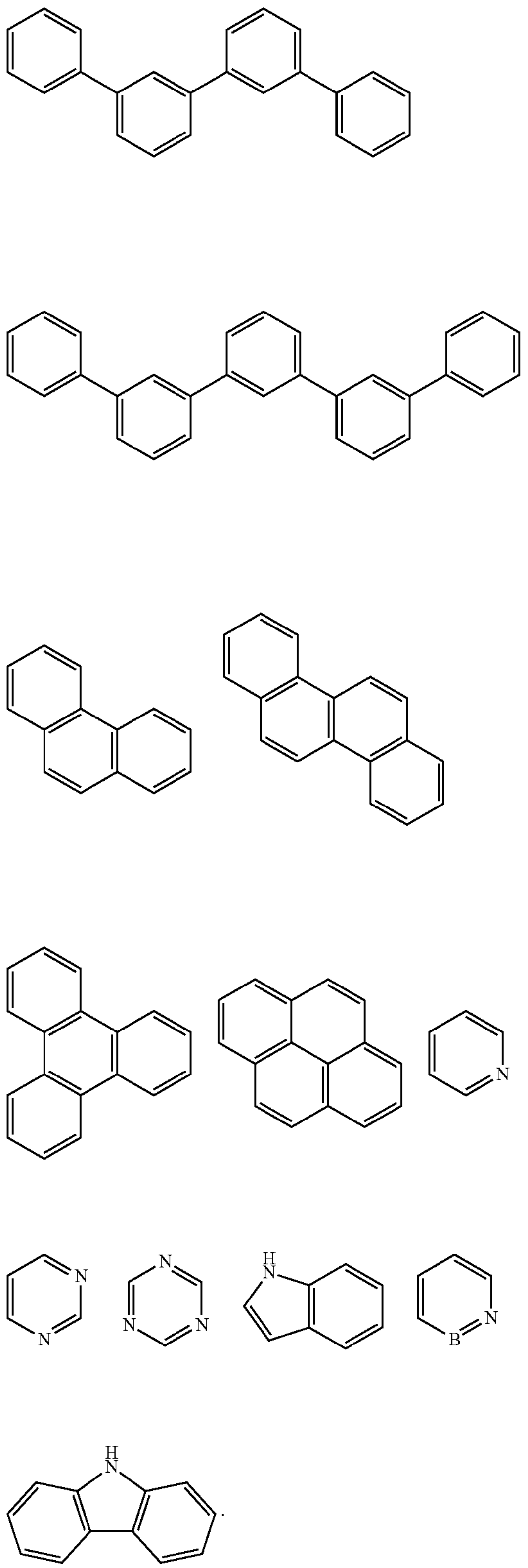

$R^1$ and $R^4$ may each independently be a substituted or unsubstituted phenyl group, and $R^5$ may be hydrogen.

X may be any one of substituted or unsubstituted selected groups from Group 3.

[Group 3]

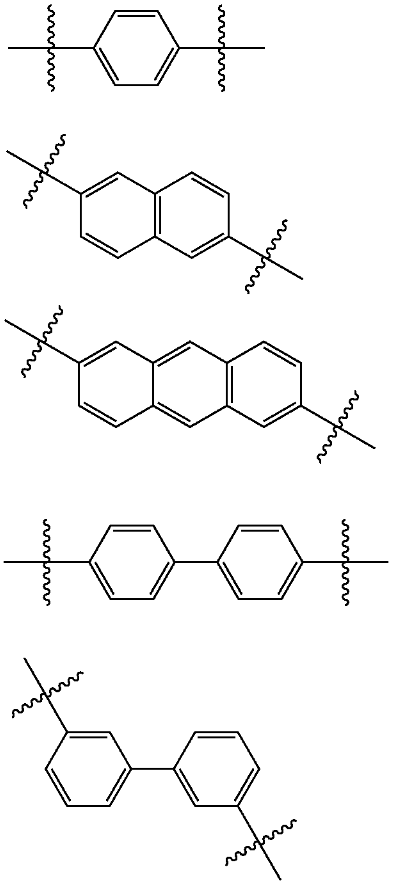

In Group 3,

is a linking point.

The group represented by Chemical Formula 2 may be represented by Chemical Formula 3 or 4.

[Chemical Formula 3]

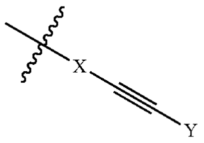

[Chemical Formula 4]

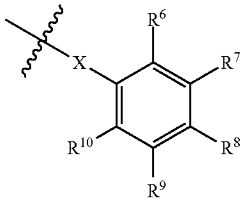

In Chemical Formula 3 and Chemical Formula 4,

X is a substituted or unsubstituted C6 to C30 arylene group,

Y is a substituted or unsubstituted C3 to C30 heteroaryl group; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof, $R^6$ to $R^{10}$ are each independently hydrogen, a substituted or unsubstituted C6 to C30 aryl group, a substituted or unsubstituted C3 to C30 heteroaryl group, or a combination thereof, at least one of $R^6$ to $R^{10}$ is a substituted or unsubstituted C3 to C30 nitrogen-containing heteroaryl group; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof, and

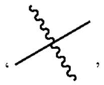

indicates a linking point with Chemical Formula 1.

Y of Chemical Formula 3 may be a substituted or unsubstituted C3 to C30 nitrogen-containing heteroaryl group selected from Group 4; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 5.

[Group 4]

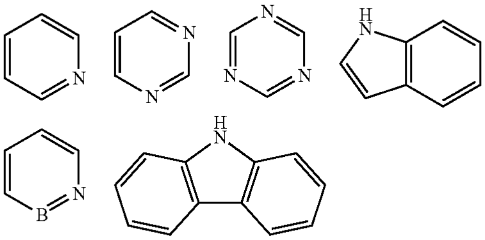

[Group 5]

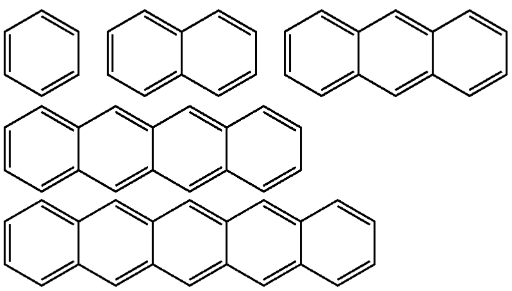

-continued

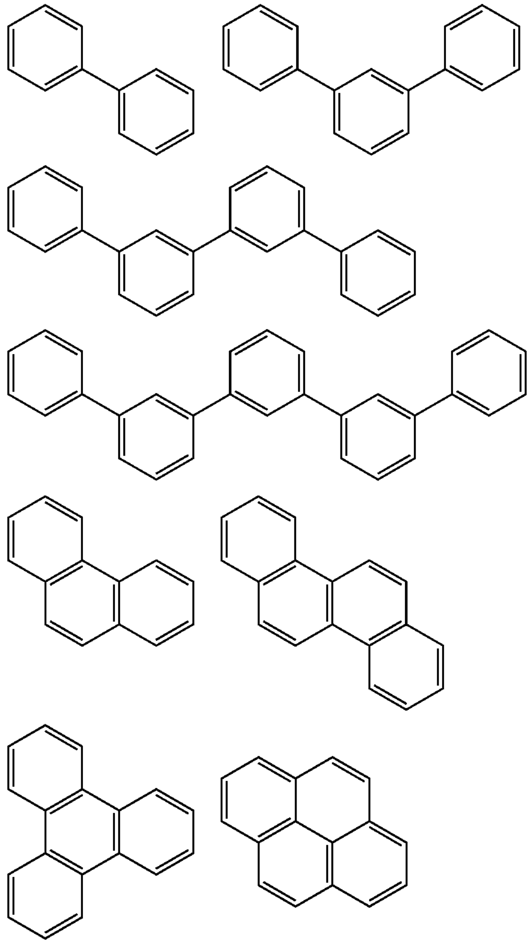

$R^6$ to $R^{10}$ of Chemical Formula 4 may each independently be a substituted or unsubstituted C3 to C30 nitrogen-containing heteroaryl group selected from Group 6 or a substituted or unsubstituted C6 to C30 aryl group selected from Group 7, and at least one of $R^7$, $R^8$, and $R^{10}$ is a substituted or unsubstituted C3 to C30 nitrogen-containing heteroaryl group selected from Group 6; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7.

[Group 6]

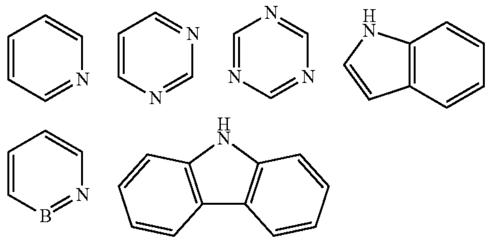

-continued

[Group 7]

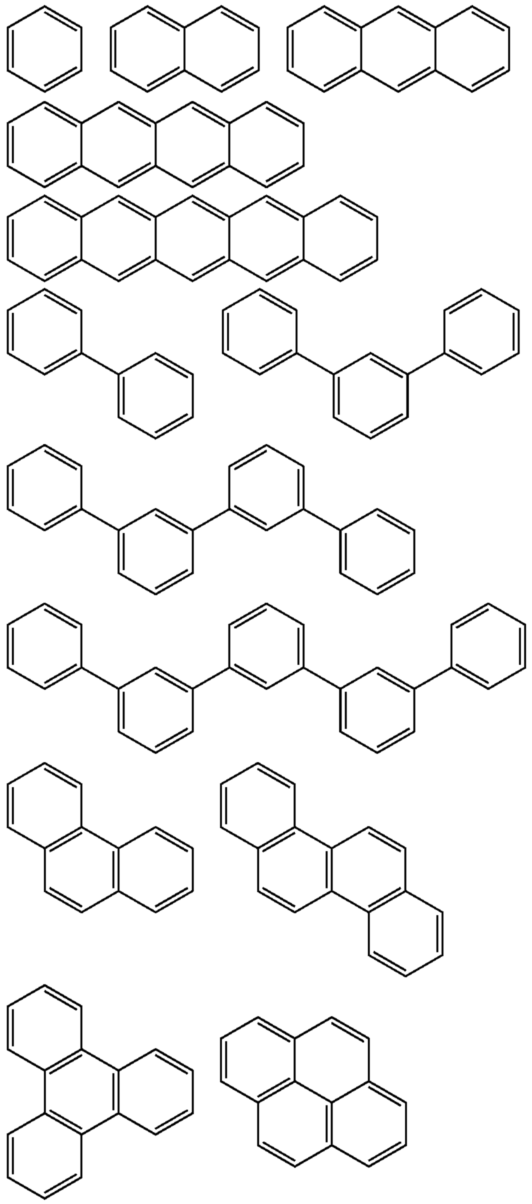

$R^6$ and $R^9$ may each independently be a substituted or unsubstituted phenyl group.

$R^8$ may be a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7, and $R^{10}$ may be a substituted or unsubstituted C3 to C30 nitrogen-containing heteroaryl group selected from Group 6; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7.

The n may be an integer satisfying the range of 2≤n≤k/2, and k may be the number of substitutable positions of A in Chemical Formula 1.

A molecular weight of the compound represented by Chemical Formula 1 may be 900 to 7,000.

The compound represented by Chemical Formula 1 may be included in an amount of 0.01 wt % to 30 wt % based on the total content of the hard mask composition.

According to another embodiment, a hardmask layer including a cured product of the hardmask composition is provided.

The cured product may include a condensed polycyclic aromatic hydrocarbon.

According to another embodiment, a pattern forming method includes applying the hardmask composition on a material layer and heat-treating the resultant to form a hardmask layer, forming a photoresist layer on the hardmask layer, exposing and developing the photoresist layer to form a photoresist pattern, selectively removing the hardmask layer using the photoresist pattern to expose a portion of the material layer, and etching an exposed portion of the material layer.

Advantageous Effects

The etch resistance of the hard mask layer may be secured.

DETAILED DESCRIPTION OF THE EMBODIMENTS

Hereinafter, example embodiments of the present disclosure will hereinafter be described in detail, and may be easily performed by a person skilled in the art. However, this disclosure may be embodied in many different forms and is not construed as limited to the example embodiments set forth herein.

In the present specification, when a definition is not otherwise provided, "substituted" refers to replacement of a hydrogen atom of a compound by a substituent selected from deuterium, a halogen atom (F, Br, Cl, or I), a hydroxyl group, a nitro group, a cyano group, an amino group, an azido group, an amidino group, a hydrazino group, a hydrazono group, a carbonyl group, a carbamyl group, a mercapto group, an ester group, a carboxyl group or a salt thereof, a sulfonic acid group or a salt thereof, a phosphoric acid group or a salt thereof, a C1 to C30 alkyl group, a C2 to C30 alkenyl group, a C2 to C30 alkynyl group, a C6 to C30 aryl group, a C7 to C30 arylalkyl group, a C1 to C30 alkoxy group, a C1 to C30 alkylthiol group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocyclic group, and a combination thereof.

In addition, two adjacent substituents of the substituted halogen atom (F, Br, Cl, or I), hydroxyl group, nitro group, cyano group, amino group, azido group, amidino group, hydrazino group, hydrazono group, carbonyl group, carbamyl group, mercapto group, ester group, carboxyl group or salt thereof, sulfonic acid group or salt thereof, phosphoric acid group or salt thereof, C1 to C30 alkyl group, C2 to C30 alkenyl group, C2 to C30 alkynyl group, C6 to C30 aryl group, C7 to C30 arylalkyl group, C1 to C30 alkoxy group, C1 to C30 alkylthiol group, C1 to C20 heteroalkyl group, C3 to C20 heteroarylalkyl group, C3 to C30 cycloalkyl group, C3 to C15 cycloalkenyl group, C6 to C15 cycloalkynyl group, and C2 to C30 heterocyclic group may be fused to form a ring. For example, the substituted C6 to C30 aryl group may be fused with another adjacent substituted C6 to C30 aryl group to form a substituted or unsubstituted fluorene ring.

In the present specification, when a definition is not otherwise provided, "hetero" refers to one including 1 to 3 heteroatoms selected from N, O, S, Se, and P.

In the present specification "aryl group" refers to a group including at least one hydrocarbon aromatic moiety, and includes hydrocarbon aromatic moieties linked by a single bond and hydrocarbon aromatic moieties fused directly or indirectly to provide a non-aromatic fused ring. The aryl group may include a monocyclic, polycyclic, or fused polycyclic (i.e., rings sharing adjacent pairs of carbon atoms) functional group.

In the present specification, "heterocyclic group" is a concept including a heteroaryl group, and may include at least one hetero atom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

More specifically, the substituted or unsubstituted aryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted terphenyl group, a substituted or unsubstituted quaterphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted fluorenyl group, a combination thereof, or a combined fused ring of the foregoing groups, but is not limited thereto.

More specifically, the substituted or unsubstituted heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, a substituted or unsubstituted dibenzothiphenyl group, a substituted or unsubstituted carbazolyl group, a pyridoindolyl group, a benzopyridooxazinyl group, a benzopyridothiazinyl group, a 9,9-dimethyl-9,10-dihydroacridinyl group, a combination thereof, or a combined fused ring of the foregoing groups, but is not limited thereto. In one example of the present invention, the heterocyclic group or the heteroaryl group may be a pyridyl group, a carbazolyl group, or a pyridoindolyl group.

Hereinafter, a hardmask composition according to an embodiment is described.

The hardmask composition according to an embodiment includes a compound and a solvent.

The compound may include a core (A) that is an aromatic moiety, and the core (A) may be substituted with a substituent (B) that is a substituted or unsubstituted aromatic moiety. The substituent (B) may be a substituted phenyl group, wherein the substituted phenyl group may include a structure in which one or more aromatic rings and/or heterocycles are linked by a single bond, an ethenylene group and/or an ethynylene group, and specifically may include a group represented by Chemical Formula 2 to be described later. Furthermore, the compound may include one or more substituted or unsubstituted C3 to C30 heteroaryl groups; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof.

As an example, the compound may be represented by Chemical Formula 1.

[Chemical Formula 1]

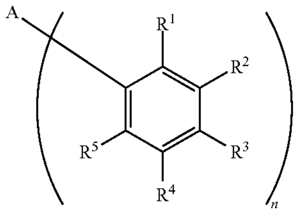

In Chemical Formula 1,

A is a C6 to C30 aromatic moiety, $R^1$ to $R^5$ are each independently hydrogen, a substituted or unsubstituted C6 to C30 aryl group, a substituted or unsubstituted C3 to C30 heteroaryl group, or a combination thereof or a group represented by Chemical Formula 2, at least one of $R^1$ to $R^5$ is a group represented by Chemical Formula 2, and n is an integer greater than or equal to 2,

[Chemical Formula 2]

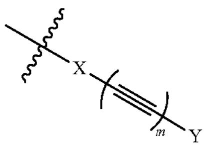

wherein, in Chemical Formula 2,

X is a substituted or unsubstituted C6 to C30 arylene group,

Y is a substituted C6 to C60 aryl group or a substituted or unsubstituted C3 to C60 heteroaryl group, wherein the substituted C6 to C60 aryl group includes a substituent selected from hydroxy group, amine group, mercapto group, a substituted or unsubstituted C1 to C30 alkoxy group, a substituted or unsubstituted C1 to C30 alkylthiol group, a substituted or unsubstituted C1 to C20 alkylamine group, a substituted or unsubstituted C3 to C30 heteroaryl group, or a combination thereof, m is 0 or 1, and

, indicates a linking point with Chemical Formula 1.

For example, the compound represented by Chemical Formula 1 may be synthesized through a Diels-Alder reaction and an elimination reaction using a compound having substituted diene and a substituted ethynyl moiety as reactants but is not limited thereto and may include a functional group which is unfavorable to the Diels-Alder reaction, for example, a hydroxy group, an amine group, a mercapto group, a substituted or unsubstituted C1 to C30 alkoxy group, a substituted or unsubstituted C1 to C30 alkylthiol group, or a substituted or unsubstituted C1 to C20 alkylamine group.

For example, the compound may be obtained from a compound containing a C≡C triple bond and cyclopentadienone, but is not limited thereto.

For example, A may be a non-condensed aromatic moiety, a condensed aromatic moiety, a moiety in which aromatic moieties are linked by a single bond, a moiety in which each ring condensed to two non-parallel sides on a benzene ring is fused, a moiety in which each ring condensed to two non-parallel sides on a benzene ring is linked by a single bond or a double bond, or a combination thereof.

For example, A may be a benzene moiety, a naphthalene moiety, an anthracene moiety, a tetracene moiety, a pentacene moiety, a biphenyl moiety, a terphenyl moiety, a quaterphenyl moiety, or a quinquephenyl moiety, a phenanthrene moiety, a pyrene moiety, a fluoranthene moiety, a benzophenanthrene moiety, a chrysene moiety, a perylene moiety, a benzopyrene moiety, a picene moiety, a benzofluoranthene moiety, a dibenzofluoranthene moiety, a benzoperylene moiety, a coronene moiety, a naphthoanthracene moiety, or a triphenylene moiety.

When the compound includes the aforementioned aromatic moiety in the core (A), the carbon content of the compound may be increased to form a hard layer, and thus high corrosion resistance may be imparted.

For example, A may be a benzene moiety or a moiety in which the benzene moieties are linked by a single bond, and may be, for example, a benzene moiety, a biphenyl moiety, an ortho-terphenyl moiety, a meta-terphenyl moiety, or a para-terphenyl moiety, but is not limited thereto.

Due to the benzene moiety or the moiety in which the benzene moieties are linked by a single bond in the core (A), a high degree of rotational freedom of the compound may be secured, solubility in a solvent is further improved due to the high degree of rotational freedom, and a hard layer may be formed to impart higher etch resistance.

For example, A may be any one selected from Group 1.

[Group 1]

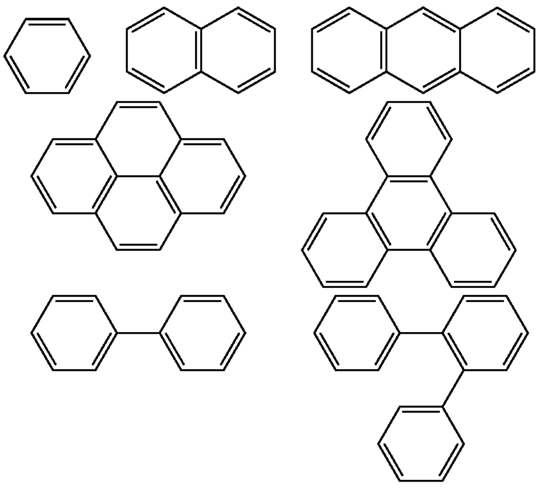

For example, A may be any one selected from Group 1-1.

[Group 1-1]

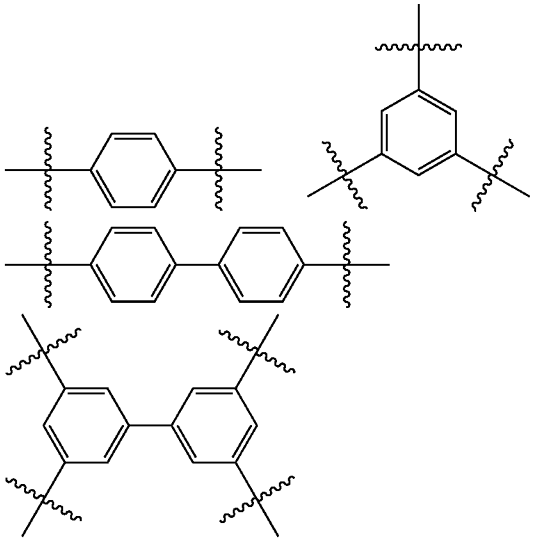

In Group 1-1,

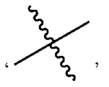

means a linking point.

The compound has a substituent (B) that is a phenyl group substituted with at least one group represented by Chemical Formula 2 in the core (A) and forms a fused structure by a reaction of an aromatic moiety of the core (A) and the substituent (B) linked thereto during the curing the compound and thus may provide a hard film layer including condensed polycyclic aromatic hydrocarbon.

The substituent (B) that is a phenyl group substituted with at least one group represented by Chemical Formula 2 linked to the core (A) may be the same as or different from each other, but may desirably be the same as each other, $R^1$ may be the same as or different from each other, but desirably may be the same as each other, $R^2$ may be the same as or different from each other, but desirably the same as each other, $R^3$ may be the same as or different from each other, but desirably the same, $R^4$ may be the same as or different from each other, $R^5$ may be the same as or different from each other, but desirably the same as each other, X may be the same or different from each other, and Y may be the same or different from each other, but desirably the same as each other.

For example, in the definition of $R^1$ to $R^5$, the "substituted" of the substituted or unsubstituted C6 to C30 aryl group and the substituted or unsubstituted C3 to C30 heteroaryl group may refer to substitution with hydroxy group, mercapto group, a C1 to C30 alkyl group, a C1 to C30 alkoxy group, a C1 to C30 alkylthiol group, a C2 to C30 alkenyl group, a C2 to C30 alkynyl group, a C6 to C30 aryl group, a C7 to C30 arylalkyl group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocyclic group, a C1 to C30 ester group, a C0 to C30 amine group, a C1 to C20 alkylamine group, a C1 to C30 thioester group, a C1 to C30 sulfone group, a halogen group, or a combination thereof.

For example, in the definitions of $R^1$ to $R^5$, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted tetracenyl group, a substituted or unsubstituted pentacenyl group, a substituted or unsubstituted biphenyl group, a substituted or unsubstituted terphenyl group, a substituted or unsubstituted quaterphenyl group, a substituted or unsubstituted quinquephenyl group, a substituted or unsubstituted phenanthrenyl group, a substituted or unsubstituted chrysenyl group, a substituted or unsubstituted picenyl group, a substituted or unsubstituted triphenylenyl group, a substituted or unsubstituted pyrenyl group, a substituted or unsubstituted fluorenyl group, a substituted or unsubstituted fluoranthenyl group, a substituted or unsubstituted acenaphthylenyl group, a substituted or unsubstituted acenaphthenyl group, a substituted or unsubstituted benzophenanthrenyl group, a substituted or unsubstituted benzofluoranthenyl group, a substituted or unsubstituted perylenyl group, a substituted or unsubstituted benzopyrenyl group, a substituted or unsubstituted naphthoanthracenyl group, a substituted or unsubstituted benzoperylenyl group, a substituted or unsubstituted dibenzopyrenyl group, a substituted or unsubstituted coronenyl group, or a combination thereof, and in the definitions of $R^1$ to $R^5$, the substituted or unsubstituted C3 to C30 heteroaryl group may be a substituted or unsubstituted pyrrolyl group, a substituted or unsubstituted indolyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothio phenyl group, a substituted or unsubstituted pyridinyl group, a substituted or unsubstituted pyrimidyl group, a substituted or unsubstituted triazinyl group, a substituted or unsubstituted imidazolyl group, a substituted or unsubstituted pyrazolyl group, a substituted or unsubstituted isoindolyl group, a substituted or unsubstituted benzimidazolyl group, a substituted or unsubstituted indazolyl group, a substituted or unsubstituted oxazolyl group, a substituted or unsubstituted thiazolyl group, or a combination thereof.

For example, in the definition of $R^1$ to $R^5$, the substituted or unsubstituted C6 to C30 aryl group may be a substituted or unsubstituted C6 to C30 condensed aryl group or a substituted or unsubstituted C6 to C30 non-condensed aryl group, but may be a substituted or unsubstituted C6 to C30 non-condensed aryl group, and in the definitions of $R^1$ to $R^5$, the substituted or unsubstituted C3 to C30 heteroaryl group may be a substituted or unsubstituted C3 to C30 condensed heteroaryl group or a substituted or unsubstituted C3 to C30 non-condensed heteroaryl group, but desirably may be a substituted or unsubstituted C3 to C30 non-condensed heteroaryl group.

Accordingly, the compound can secure a high degree of rotational freedom, and may have improved solubility in a solvent due to the high degree of rotational freedom, and may provide a hard layer to impart higher etch resistance.

For example, in the definitions of $R^1$ to $R^5$, the substituted or unsubstituted C3 to C30 heteroaryl group may include at least one nitrogen.

For example, in the definitions of $R^1$ to $R^5$, the substituted or unsubstituted C3 to C30 heteroaryl group may include one nitrogen, two nitrogens, or three nitrogens.

For example, $R^1$ to $R^5$ may each independently be hydrogen or a substituted or unsubstituted group selected from Group 2.

[Group 2]

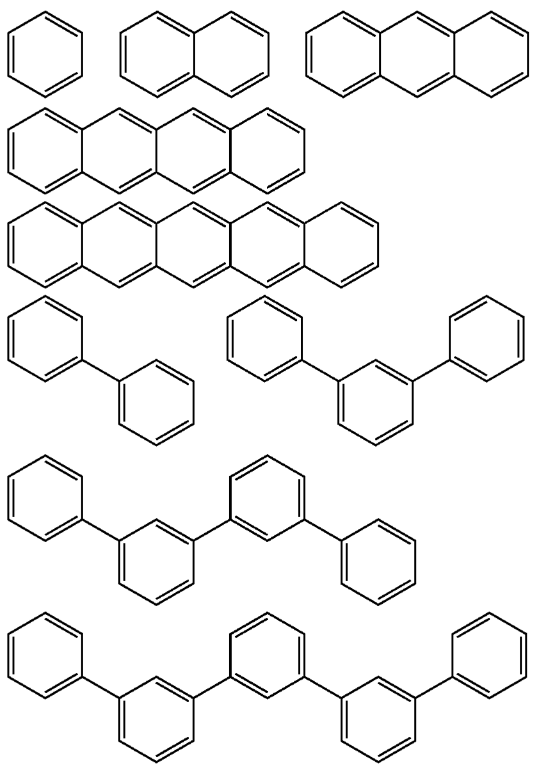

-continued

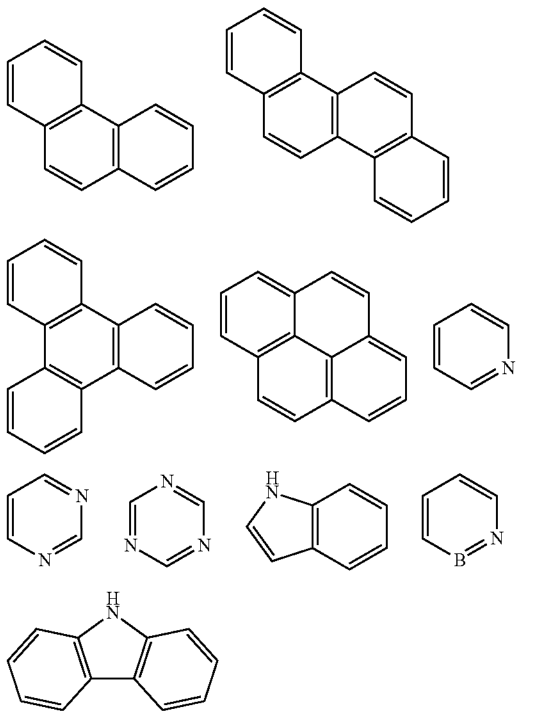

For example, $R^1$ to $R^5$ may each independently be hydrogen or a substituted or unsubstituted group selected from Group 2-1.

[Group 2-1]

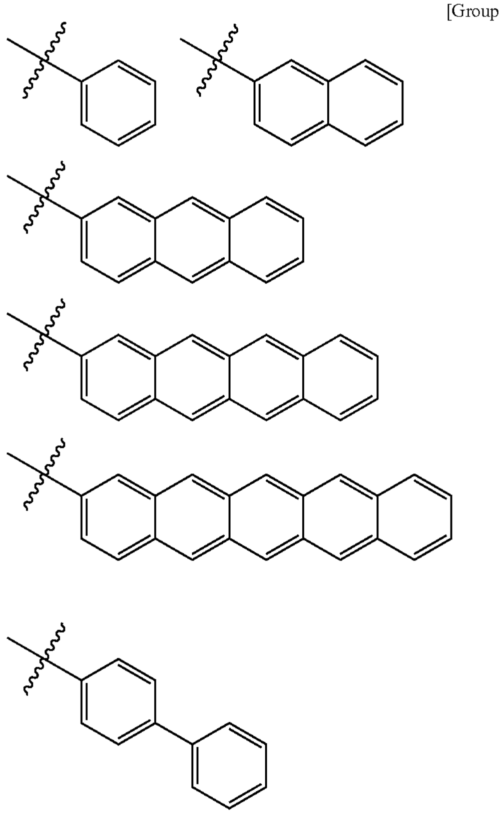

-continued

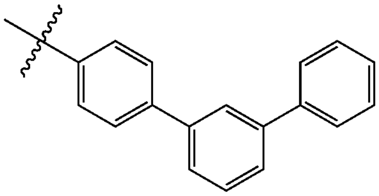

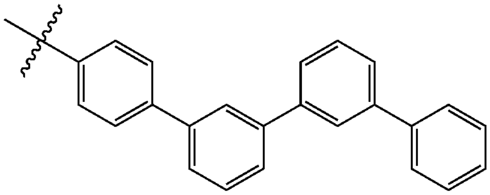

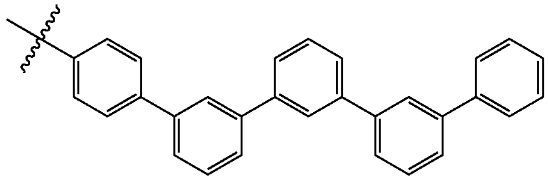

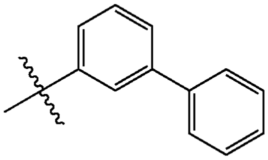

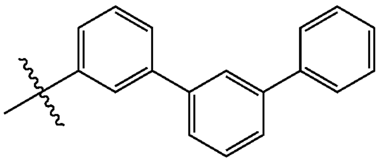

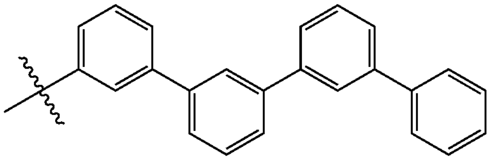

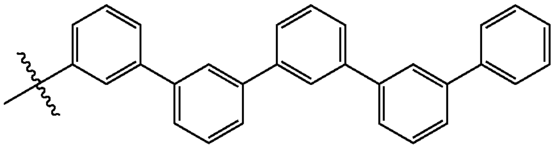

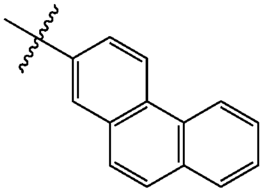

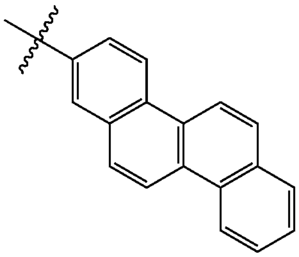

-continued

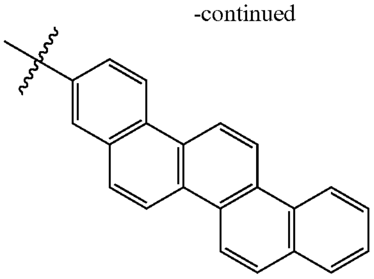

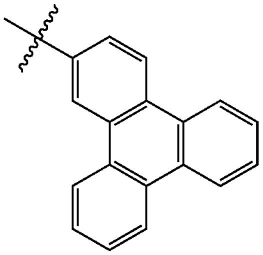

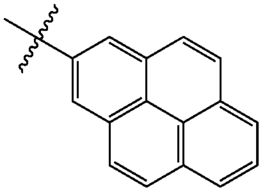

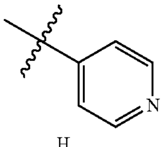 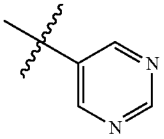 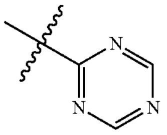

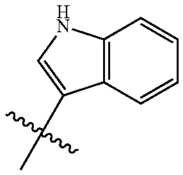 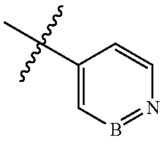

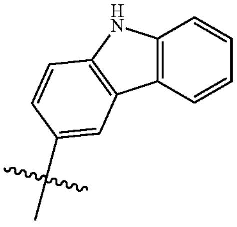

In Group 2-1,

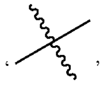

means a linking point.

In Group 2 and Group 2-1, each group may be unsubstituted or substituted with one or more substituents. Herein the substituent may be for example a hydroxy group, a mercapto group, a C1 to C30 alkyl group, a C1 to C30 alkoxy group, a C1 to C30 alkylthiol group, a C2 to C30 alkenyl group, a C2 to C30 alkynyl group, a C6 to C30 aryl group, a C7 to C30 arylalkyl group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocyclic group, a C1 to C30 ester group, a C0 to C30 amine group, a C1 to C20 alkylamine group, a C1 to C30 thioester group, a C1 to C30 sulfone group, a halogen, or a combination thereof.

For example, $R^1$, $R^2$, $R^4$, and $R^5$ may each independently be hydrogen, a substituted or unsubstituted C6 to C30 aryl group, a substituted or unsubstituted C3 to C30 heteroaryl group, or a combination thereof.

For example, $R^1$, $R^2$, $R^4$, and $R^5$ may each independently be hydrogen, a substituted or unsubstituted phenyl group, a substituted or unsubstituted naphthyl group, a substituted or unsubstituted anthracenyl group, a substituted or unsubstituted biphenyl group, a substituted or unsubstituted terphenyl group, a substituted or unsubstituted phenanthrenyl group, a substituted or unsubstituted fluorenyl group, a substituted or unsubstituted acenaphthylenyl group, a substituted or unsubstituted acenaphthenyl group, or a combination thereof.

For example, at least one of $R^1$ to $R^5$ may be a substituted or unsubstituted phenyl group, for example, 1 to 3 of $R^1$ to $R^5$ may be a substituted or unsubstituted phenyl group, for example, one or two of $R^1$ to $R^5$ may be a substituted or unsubstituted phenyl group.

For example, $R^1$ and $R^4$ may each independently be a substituted or unsubstituted phenyl group, but desirably an unsubstituted phenyl group.

For example, at least one of $R^1$ to $R^5$ may be hydrogen.

For example, $R^5$ may be hydrogen.

For example, $R^1$ and $R^4$ may each independently be a substituted or unsubstituted phenyl group, and $R^5$ may be hydrogen.

As described above, at least one of $R^1$ to $R^5$ may be a group represented by Chemical Formula 2. Accordingly, since the compound includes a hydrophilic functional group and secures a high degree of rotational freedom, even though the compound has a high molecular weight, dissolubility of the compound in a solvent may be increased. In addition, the compound includes a plurality of aromatic moieties, which may increase a carbon content, and thereby, may provide higher etch resistance.

For example, $R^3$ may be a group represented by Chemical Formula 2. Since $R^3$ is the group represented by Chemical Formula 2, the compound may not only secure a higher degree of rotational freedom but also forms a harder layer during the curing, providing much higher etch resistance.

For example, $R^1$, $R^2$, $R^4$, and $R^5$ may each independently be hydrogen or a substituted or unsubstituted group selected from Group 2, and $R^3$ may be the group represented by Chemical Formula 2.

For example, $R^1$, $R^2$, $R^4$, and $R^5$ may each independently be hydrogen or a substituted or unsubstituted group selected from Group 2-1, and $R^3$ may be the group represented by Chemical Formula 2.

For example, $R^1$, $R^2$, $R^4$, and $R^5$ may each independently be hydrogen, a substituted or unsubstituted phenyl group, a substituted or unsubstituted naphthyl group, a substituted or unsubstituted anthracenyl group, a substituted or unsubstituted biphenyl group, a substituted or unsubstituted terphenyl group, a substituted or unsubstituted phenanthrenyl group, a substituted or unsubstituted fluorenyl group, a substituted or unsubstituted acenaphthylenyl group, a substituted or unsubstituted acenaphthenyl group, or a combination thereof, and $R^3$ may be the group represented by Chemical Formula 2.

For example, $R^1$ and $R^4$ may each independently be a substituted or unsubstituted phenyl group, $R^5$ may be hydrogen, and $R^3$ may be the group represented by Chemical Formula 2.

For example, X may be a substituted or unsubstituted C6 to C30 arylene group, and desirably an unsubstituted C6 to C30 arylene group as described above.

For example, X may be a substituted or unsubstituted phenylene group, a substituted or unsubstituted naphthylene group, a substituted or unsubstituted anthracenylene group, a substituted or unsubstituted tetracenylene group, a substituted or unsubstituted pentacenylene group, a substituted or unsubstituted biphenylene group, a substituted or unsubstituted terphenylene group, a substituted or unsubstituted quaterphenylene group, a substituted or unsubstituted quinquephenylene group, or a combination thereof.

For example, X may be any one substituted or unsubstituted selected from Group 3, and in Group 3, each moiety may be unsubstituted or substituted with one or more substituents.

[Group 3]

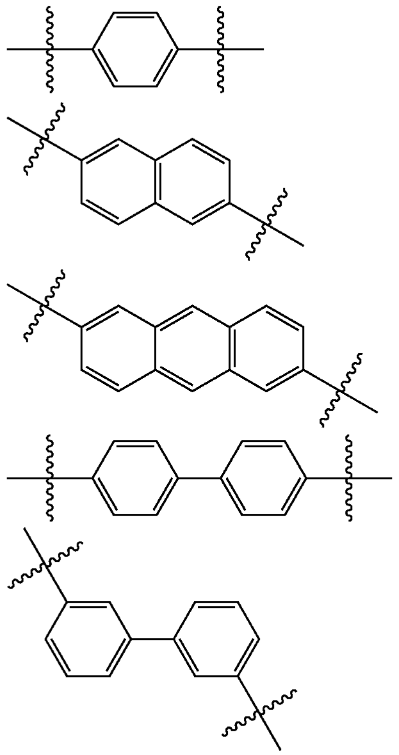

In Group 3,

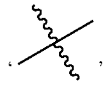

means a linking point.

For example, in the definition of Y, "the substituted" of the substituted C6 to C60 aryl group and a substituted or unsubstituted C3 to C60 heteroaryl group may refer to substitution with a hydroxy group, a mercapto group, a C1 to C30 alkyl group, a C1 to C30 alkoxy group, a C1 to C30 alkylthiol group, a C2 to C30 alkenyl group, a C2 to C30 alkynyl group, a C6 to C30 aryl group, a C7 to C30 arylalkyl group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocyclic group, a C1 to C30 ester group, a C0 to C30 amine group, a C1 to C20 alkylamine group, a C1 to C30 thioester group, a C1 to C30 sulfone group, a halogen, or a combination thereof.

Specifically, In the definition of Y, the substituted C6 to C60 aryl group may include at least one substituent which is selected from hydroxy group, amine group, mercapto group, substituted or unsubstituted methoxy group, a substituted or unsubstituted ethoxy group, substituted or unsubstituted propoxy group, substituted or unsubstituted butoxy group, substituted or unsubstituted pyrrolyl group, substituted or unsubstituted indolyl group, substituted or unsubstituted carbazolyl group, substituted or unsubstituted pyridinyl group, substituted or unsubstituted pyridmidyl group, substituted or unsubstituted triazinyl group, substituted or unsubstituted imidazolyl group, substituted or unsubstituted pyrazolyl group, substituted or unsubstituted isoindolyl group, a substituted or unsubstituted benzimidazolyl group, a substituted or unsubstituted indazolyl group, a substituted or unsubstituted oxazolyl group, a substituted or unsubstituted thiazolyl group, or a combination thereof.

Accordingly, dissolubility of the compound for a solvent may be increased, so that the compound may be more effectively applied to a solution process such as spin coating, and when coated and cured, affinity for an underlying film increases, film flatness of a film formed therefrom may not only be much improved, but also the film may exhibit high etch resistance to etching gas to which exposed during the subsequent process such as an etching process.

For example, in the definition of Y, the substituted or unsubstituted C3 to C60 heteroaryl group may be a substituted or unsubstituted C3 to C40 heteroaryl group or a substituted or unsubstituted C3 to C30 heteroaryl group, and may be, specifically, selected from a substituted or unsubstituted pyrrolyl group, a substituted or unsubstituted indolyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted pyridinyl group, a substituted or unsubstituted pyridmidyl group, a substituted or unsubstituted triazinyl group, a substituted or unsubstituted imidazolyl group, a substituted or unsubstituted pyrazolyl group, a substituted or unsubstituted isoindolyl group, a substituted or unsubstituted benzimidazolyl group, a substituted or unsubstituted indazolyl group, a substituted or unsubstituted oxazolyl group, a substituted or unsubstituted thiazolyl group, or a combination thereof, but is not limited thereto.

For example, in the definition of Y, the substituted C6 to C60 aryl group may be a substituted C6 to C40 aryl group or a substituted C6 to C30 aryl group and may be, specifically, selected from a substituted phenyl group, a substituted naphthyl group, a substituted anthracenyl group, a substituted tetracenyl group, a substituted pentacenyl group, a substituted biphenyl group, a substituted terphenyl group, a substituted quaterphenyl group, a substituted quinquephenyl group, a substituted phenanthrenyl group, a substituted chrysenyl group, a substituted picenyl group, a substituted triphenylenyl group, a substituted pyrenyl group, a substituted fluorenyl group, a substituted fluoranthenyl group, a substituted acenaphthylenyl group, a substituted acenaphthenyl group, a substituted benzophenanthrenyl group, a substituted benzofluoranthenyl group, a substituted perylenyl group, a substituted benzopyrenyl group, a substituted naphthoanthracenyl group, a substituted benzoperylenyl group, a substituted dibenzopyrenyl group, a substituted coronenyl group or combination thereof, but is not limited thereto.

For example, in the definition of Y, the substituted C6 to C60 aryl group may be a condensed cycle or a non-condensed cycle and the substituted or unsubstituted C3 to C60 heteroaryl group may be a condensed heterocycle or non-condensed heterocycle.

For example, in the definition of Y, the substituted or unsubstituted C3 to C60 heteroaryl group may include at least one nitrogen.

For example, in the definition of Y, the substituted or unsubstituted C3 to C60 heteroaryl group may include one nitrogen, two nitrogens, or three nitrogens.

For example, in the definition of Y, the substituted or unsubstituted C3 to C60 heteroaryl group may be any substituted or unsubstituted group selected from Group 4, and the substituted C6 to C60 aryl group may be any substituted one selected from Group 5.

[Group 4]

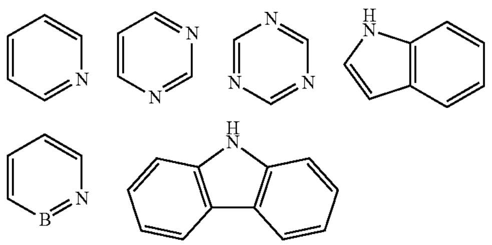

[Group 5]

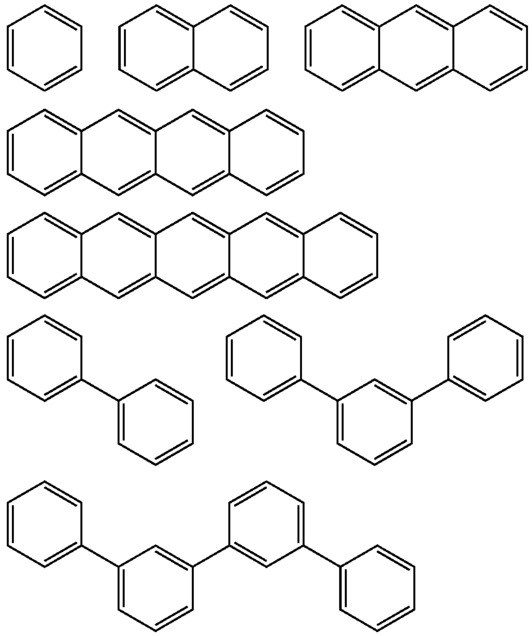

-continued
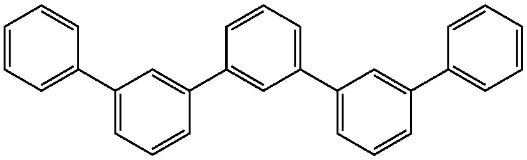
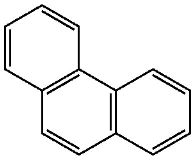
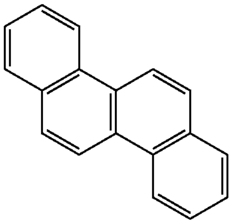
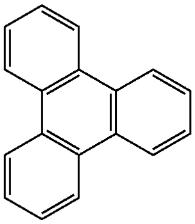
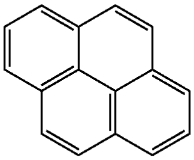
For example, in Y, the substituted or unsubstituted C3 to C60 heteroaryl group may be any substituted or unsubstituted group selected from Group 4-1, and the substituted C6 to C60 aryl group may be any substituted one selected from Group 5-1.
[Group 4-1]
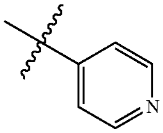
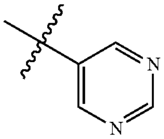
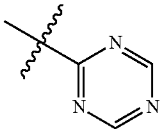
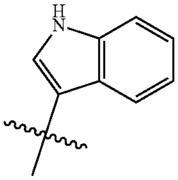
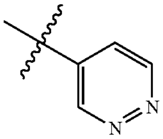
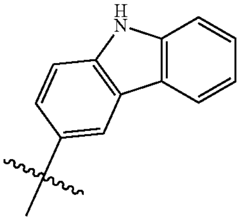
[Group 5-1]
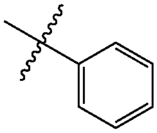
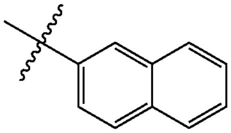
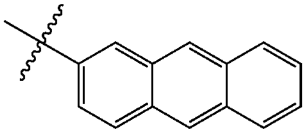
-continued
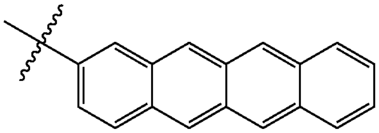
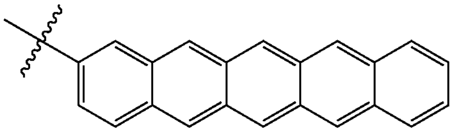
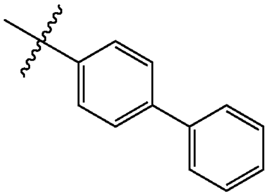
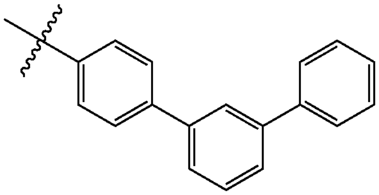
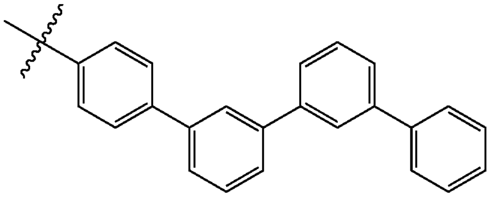
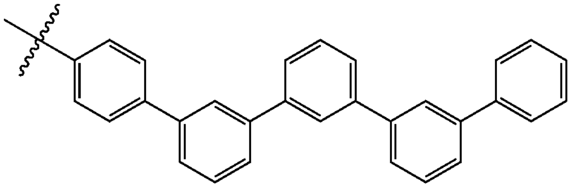
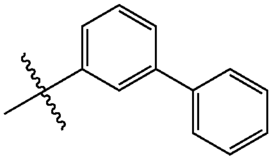
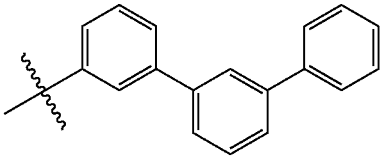
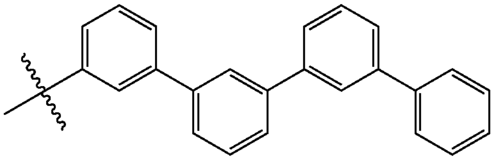
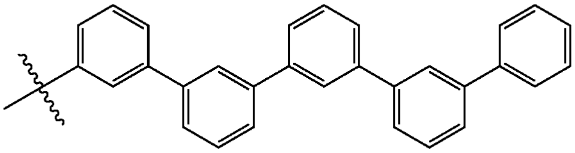

-continued

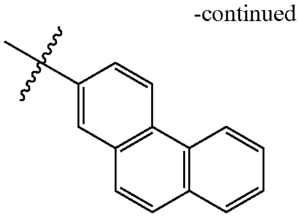

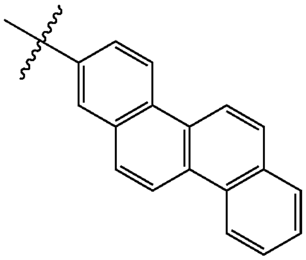

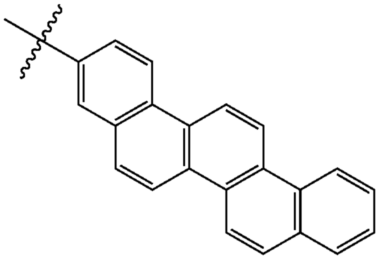

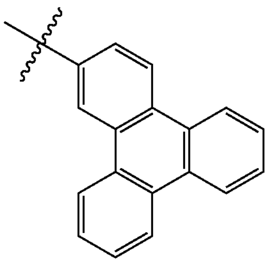

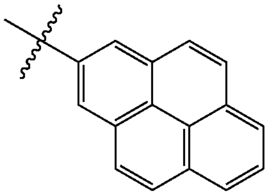

In Group 4-1 and Group 5-1,

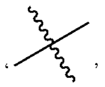

means a linking point.

For example, the group represented by Chemical Formula 2 may be represented by Chemical Formula 3 or 4.

[Chemical Formula 3]

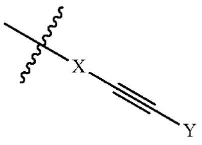

-continued

[Chemical Formula 4]

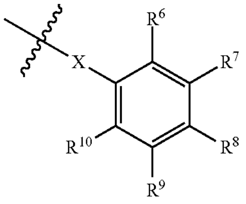

In Chemical Formula 3 and Chemical Formula 4, X and Y are the same as described above, $R^6$ to $R^{10}$ are each independently hydrogen, a substituted or unsubstituted C6 to C30 aryl group, a substituted or unsubstituted C3 to C30 heteroaryl group, or a combination thereof, at least one of $R^6$ to $R^{10}$ is a substituted or unsubstituted C3 to C30 nitrogen-containing heteroaryl group; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof, and

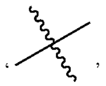

indicates a linking point with Chemical Formula 1.

For example, Y of Chemical Formula 3 may be a substituted or unsubstituted C3 to C30 heteroaryl group; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof.

For example, Y of Chemical Formula 3 may be a substituted or unsubstituted C3 to C30 nitrogen-containing heteroaryl group selected from Group 4; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 5.

For example, Y of Chemical Formula 3 may be a substituted or unsubstituted C3 to C30 nitrogen-containing heteroaryl group selected from Group 4-1; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 5-1.

For example, Y of Chemical Formula 3 may be a substituted or unsubstituted C3 to C30 heteroaryl group; or a C6 to C30 aryl group substituted with a hydroxy group, an amine group, a mercapto group, a substituted or unsubstituted methoxy group, a substituted or unsubstituted ethoxy group, a substituted or unsubstituted propoxy group, a substituted or unsubstituted butoxy group, or a combination thereof.

In Chemical Formula 4, at least one of $R^6$ to $R^{10}$ includes a substituted or unsubstituted C3 to C30 nitrogen-containing heteroaryl group; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof, and thereby dissolubility in a solvent be further improved and a harder layer may be provided when the compound is cured.

For example, in the definintion of $R^6$ to $R^{10}$ of Chemical Formula 4, the "substituted" of the substituted or unsubstituted C6 to C30 aryl group and a substituted or unsubstituted C3 to C30 heteroaryl group may refer to substitution with hydroxy group, mercapto group, a C1 to C30 alkyl group, a C1 to C30 alkoxy group, a C1 to C30 alkylthiol group, a C2 to C30 alkenyl group, a C2 to C30 alkynyl group, a C6 to C30 aryl group, a C7 to C30 arylalkyl group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocyclic group, a C1 to C30 ester group, a C0 to C30 amine group, a C1 to C20 alkylamine group, a C1 to C30 thioester group, a C1 to C30 sulfone group, a halogen, or a combination thereof.

For example, in the definintion of $R^6$ to $R^{10}$ of Chemical Formula 4, the substituted or unsubstituted C6 to C30 aryl group may be selected from a substituted or unsubstituted phenyl group, a substituted or unsubstituted naphthyl group, a substituted or unsubstituted anthracenyl group, a substituted or unsubstituted tetracenyl group, a substituted or unsubstituted pentacenyl group, a substituted or unsubstituted biphenyl group, a substituted or unsubstituted terphenyl group, a substituted or unsubstituted quaterphenyl group, a substituted or unsubstituted quinquephenyl group, a substituted or unsubstituted phenanthrenyl group, a substituted or unsubstituted chrysenyl group, a substituted or unsubstituted picenyl group, a substituted or unsubstituted triphenylenyl group, a substituted or unsubstituted pyrenyl group, a substituted or unsubstituted fluorenyl group, a substituted or unsubstituted fluoranthenyl group, a substituted or unsubstituted acenaphthylenyl group, a substituted or unsubstituted acenaphthenyl group, a substituted or unsubstituted benzophenanthrenyl group, a substituted or unsubstituted benzofluoranthenyl group, a substituted or unsubstituted perylenyl group, a substituted or unsubstituted benzopyrenyl group, a substituted or unsubstituted naphthoanthracenyl group, a substituted or unsubstituted benzoperylenyl group, a substituted or unsubstituted dibenzopyrenyl group, a substituted or unsubstituted coronenyl group, or a combination thereof, and in the definition of $R^6$ to $R^{10}$ of Chemical Formula 4, the substituted or unsubstituted C3 to C30 heteroaryl group may be selected from a substituted or unsubstituted pyrrolyl group, a substituted or unsubstituted indolyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted pyridinyl group, a substituted or unsubstituted pyridmidyl group, a substituted or unsubstituted triazinyl group, a substituted or unsubstituted imidazolyl group, a substituted or unsubstituted pyrazolyl group, a substituted or unsubstituted isoindolyl group, a substituted or unsubstituted benzimidazolyl group, a substituted or unsubstituted indazolyl group, a substituted or unsubstituted oxazolyl group, a substituted or unsubstituted thiazolyl group, or a combination thereof.

For example, in the definintion of $R^6$ to $R^{10}$ of Chemical Formula 4, the substituted or unsubstituted C6 to C30 aryl group may be a substituted or unsubstituted C6 to C30 condensed aryl group or a substituted or unsubstituted C6 to C30 non-condensed aryl group and the substituted or unsubstituted C3 to C30 heteroaryl group may be a substituted or unsubstituted C3 to C30 condensed heteroaryl group or a substituted or unsubstituted C3 to C30 non-condensed heteroaryl group.

For example, in the definintion of $R^6$ to $R^{10}$ of Chemical Formula 4, the substituted or unsubstituted C3 to C30 heteroaryl group may include at least one nitrogen.

For example, in the definintion of $R^6$ to $R^{10}$ of Chemical Formula 4, the substituted or unsubstituted C3 to C30 heteroaryl group may include one nitrogen, two nitrogens, or three nitrogens.

For example, in the definition of $R^6$ to $R^{10}$ of Chemical Formula 4, the substituted or unsubstituted C3 to C30 heteroaryl group may be a C3 to C30 nitrogen-containing heteroaryl group selected from Group 6, and the substituted or unsubstituted C6 to C30 aryl group may be a C6 to C30 aryl group selected from Group 7.

[Group 6]

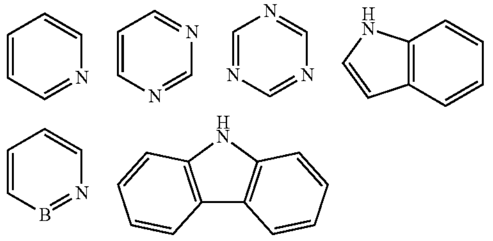

[Group 7]

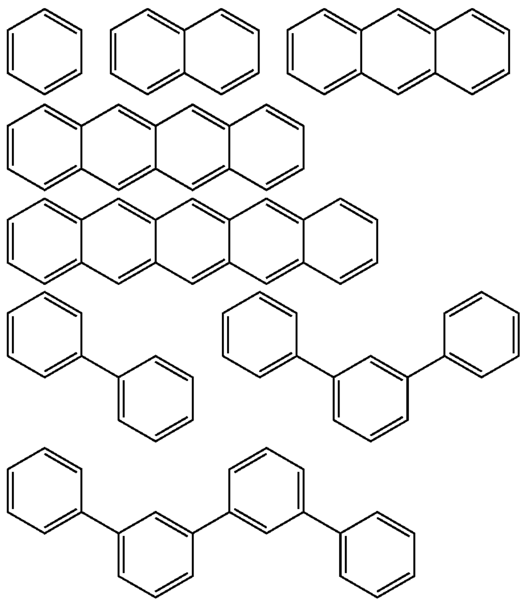

-continued
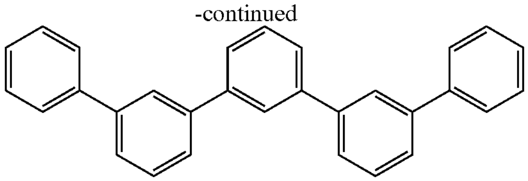
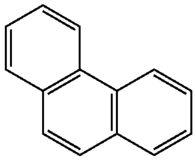
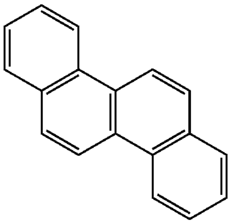
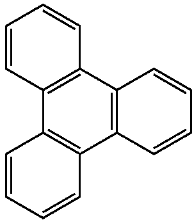
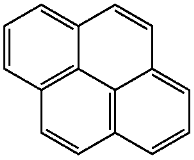
For example, in the definition of $R^6$ to $R^{10}$ of Chemical Formula 4, the substituted or unsubstituted C3 to C30 heteroaryl group may be a C3 to C30 nitrogen-containing heteroaryl group selected from Group 6-1, and the substituted or unsubstituted C1 to C30 aryl group may be a C6 to C30 aryl group selected from Group 7-1.
[Group 6-1]
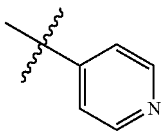
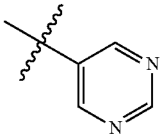
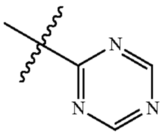
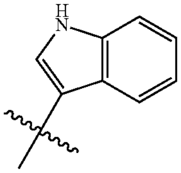
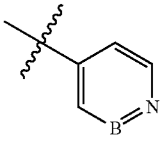
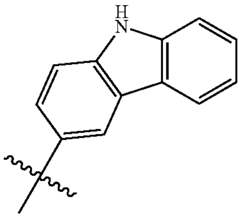
[Group 7-1]
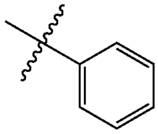
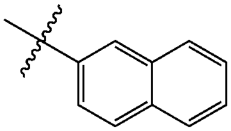
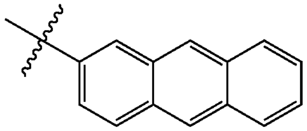
-continued
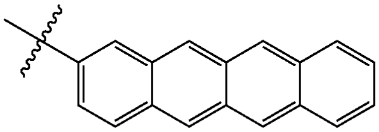
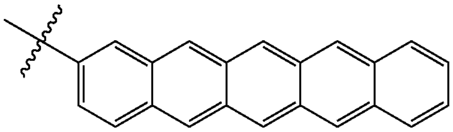
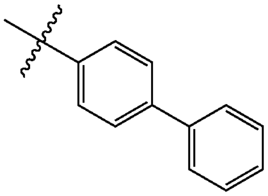
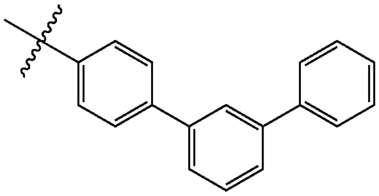
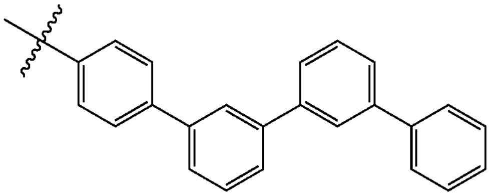
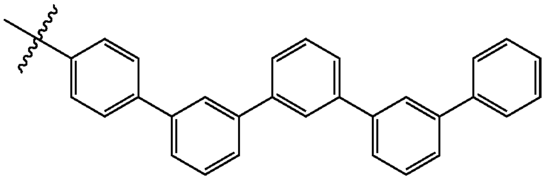
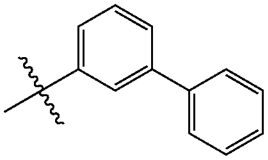
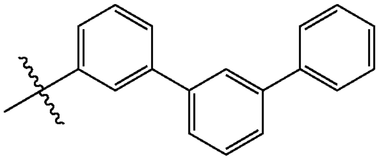
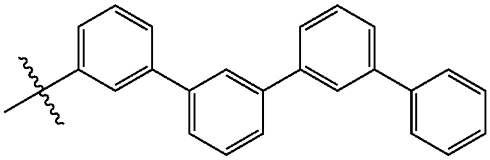
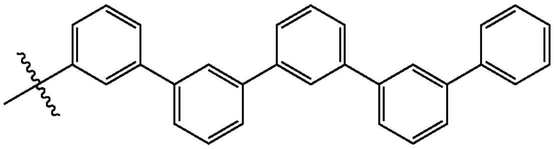

-continued

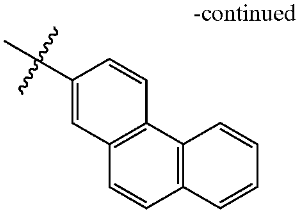

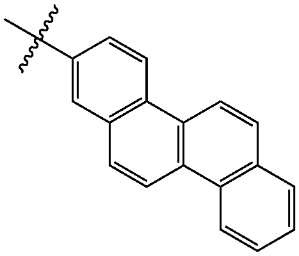

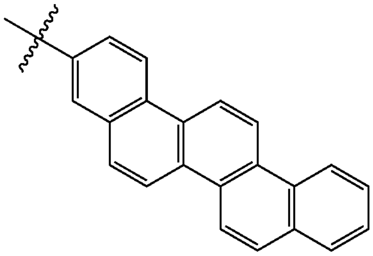

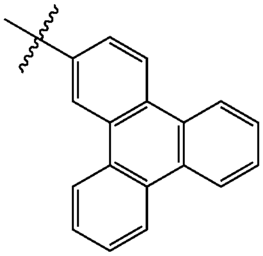

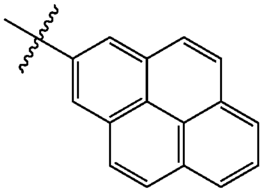

In Groups 6-1 and 7-1

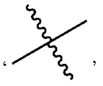

means a linking point.

In Groups 6, 7, 6-1, and 7-1, each group may be unsubstituted or substituted with one or more substituents.

For example, at least one of $R^7$, $R^8$, and $R^{10}$ in Chemical Formula 4 may be a substituted or unsubstituted C3 to C30 heteroaryl group; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof.

For example, $R^6$ to $R^{10}$ of Chemical Formula 4 may each independently be a substituted or unsubstituted C3 to C30 nitrogen-containing heteroaryl group selected from Group 6 or a substituted or unsubstituted C1 to C30 aryl group from Group 7, and in Chemical Formula 4, at least one of $R^7$, $R^8$, and $R^{10}$ may be a substituted or unsubstituted C3 to C30 nitrogen-containing heteroaryl group selected from Group 6; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7.

For example, $R^6$ to $R^{10}$ in Chemical Formula 4 may each independently be a substituted or unsubstituted C3 to C30 nitrogen-containing heteroaryl group selected from Group 6-1, or a substituted or unsubstituted C6 to C30 aryl group selected from Group 7-1, and in Chemical Formula 4, at least one of $R^7$, $R^8$, and $R^{10}$ may be a substituted or unsubstituted C3 to C30 nitrogen-containing heteroaryl group selected from Group 6-1; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7-1.

For example, $R^8$ of Chemical Formula 4 may be a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7, and $R^{10}$ of Chemical Formula 4 may be a substituted or unsubstituted C3 to C30 nitrogen-containing heteroaryl group selected from Group 6; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7.

For example, $R^8$ of Chemical Formula 4 may be a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7-1, and $R^{10}$ of Chemical Formula 4 may be a substituted or unsubstituted C3 to C30 nitrogen-containing heteroaryl group selected from Group 6-1; or a C6 to C30 aryl group substituted with a hydroxy group, an amine group, a mercapto group, a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7-1.

For example, $R^8$ of Chemical Formula 4 may be a methoxyphenyl group, a methoxynaphthyl group, a methoxyanthracenyl group, a methoxybiphenyl group, a methoxytriphenyl group, or a methoxyphenanthrenyl group, and $R^{10}$ of Chemical Formula 4 may be a pyrrolyl group, an imidazolyl group, a pyrazolyl group, a pyridinyl group, a pyrimidinyl group, a methoxyphenyl group, a methoxynaphthyl group, a methoxyanthracenyl group, a methoxybiphenyl group, a methoxytriphenyl group, or a methoxyphenanthrenyl group.

For example, in Chemical Formula 4, at least one of $R^6$ to $R^{10}$ may be a substituted or unsubstituted phenyl group, for example, one to three of $R^6$ to $R^{10}$ may be a substituted or unsubstituted phenyl group, for example, one or two of $R^6$ to $R^{10}$ may be a substituted or unsubstituted phenyl group.

For example, $R^6$ and $R^9$ in Chemical Formula 4 may each independently be a substituted or unsubstituted phenyl group, but desirably an unsubstituted phenyl group.

For example, in Chemical Formula 4, all of $R^6$ to $R^{10}$ may not be hydrogen, or only one may be hydrogen, and desirably all of $R^6$ to $R^{10}$ may not be hydrogen. Accordingly, since the carbon content of the compound may be further increased, a hard layer may be formed, and thus high etch resistance may be imparted.

For example, $R^6$ to $R^{10}$ of Chemical Formula 4 may each independently be present or two adjacent ones may be linked to each other to form a ring, and specifically, two adjacent ones of $R^1$ to $R^5$ may be linked by a single bond or a double bond, or two adjacent ones may be fused to form rings.

For example, $R^7$ and $R^8$ of Chemical Formula 4 may each independently exist, be linked by a single bond or a double bond, or two adjacent ones may be fused to form a ring.

For example, n may be an integer satisfying the range of $2 \leq n \leq k/2$, and k may be the number of substitutable positions of A in Chemical Formula 1.

For example, when A is a substituted or unsubstituted benzene moiety, n may be 2 or 3, when A is a substituted or unsubstituted naphthalene moiety, n may be an integer of 2 or more and 4 or less, when A is a substituted or unsubstituted anthracene moiety, n may be an integer of 2 or more and 5 or less, when A is a substituted or unsubstituted pyrene moiety, n may be an integer of 2 or more and 5 or less, when A is a substituted or unsubstituted triphenylene moiety, n may be an integer of 2 or more and 6 or less, when A is a substituted or unsubstituted biphenyl moiety, n may be an integer of 2 or more and 5 or less, and when A is a substituted or unsubstituted terphenyl moiety, n may be 2 an integer of 2 or more and 7 or less.

For example, A may be an integer of 2 to 4, 3 or 4.

The aforementioned compound may have, for example, a molecular weight of about 900 to 7,000 g/mol, about 1,000 to 6,000 g/mol, or about 1,500 to 5,000 g/mol but is not limited thereto.

In general, when a compound including a plurality of aromatic moieties but having a molecular weight within the ranges is used, formation of pin-holes and voids or degradation of thickness distribution may occur during the baking process, failing in obtaining a uniform thin film, but the compound represented by Chemical Formula 1 has a molecular weight within the ranges but may form a more uniform thin film with neither the formation of pin-holes and voids nor the degradation of thickness distribution during the baking process. In addition, since the thin film is formed as a hard layer, the thin film may exhibit high etch resistance to etching gas to which exposed in the subsequent process such as an etching process.

On the other hand, the solvent used in the hardmask composition may be anyone having sufficient dissolubility or dispersibility regarding the compound and may include for example at least one selected from propylene glycol, propylene glycol diacetate, methoxy propanediol, diethylene glycol, diethylene glycol butyl ether, tri(ethylene glycol) monomethyl ether, propylene glycol monomethylether, propylene glycol monomethylether acetate, cyclohexanone, ethyllactate, gamma-butyrolactone, N,N-dimethyl formamide, N,N-dimethyl acetamide, methylpyrrolidone, methylpyrrolidinone, acetylacetone, and ethyl 3-ethoxypropionate, but is not limited thereto.

The compound may be for example included in an amount of about 0.01 to 30 wt %, for example about 1 to 25 wt %, about 3 to 20 wt %, or about 5 to 15 wt % based on the total amount of the hardmask composition. When the compound is included within the ranges, a thickness, surface roughness, and planarization of the hardmask may be controlled.

The hardmask composition may further include an additive of a surfactant, a crosslinking agent, a thermal acid generator, or a plasticizer.

The surfactant may include for example a fluoroalkyl-based compound, an alkylbenzene sulfonate salt, an alkyl pyridinium salt, polyethylene glycol, or a quaternary ammonium salt, but is not limited thereto.

The crosslinking agent may be, for example, a melamine-based, substituted urea-based, or a polymer-based crosslinking agent. Desirably, it may be a crosslinking agent having at least two crosslinking forming substituents, for example, a compound such as methoxymethylated glycoluril, butoxymethylated glycoluril, methoxymethylated melamine, butoxymethylated melamine, methoxymethylated benzoguanamine, butoxymethylated benzoguanamine, methoxymethylatedurea, butoxymethylatedurea, methoxymethylated thiourea, or butoxymethylated thiourea, and the like.

The crosslinking agent may be a crosslinking agent having high heat resistance. The crosslinking agent having high heat resistance may be a compound including a crosslinking substituent including an aromatic ring (for example a benzene ring, or a naphthalene ring) in the molecule.

The thermal acid generator may be for example an acidic compound such as p-toluene sulfonic acid, trifluoromethane sulfonic acid, pyridiniump-toluenesulfonic acid, salicylic acid, sulfosalicylic acid, citric acid, benzoic acid, hydroxybenzoic acid, naphthalenecarbonic acid, and the like or/and 2,4,4,6-tetrabromocyclohexadienone, benzointosylate, 2-nitrobenzyltosylate, other organosulfonic acid alkylester, and the like, but is not limited thereto.

The additive may be included in an amount of about 0.001 to 10 parts by weight, about 0.01 to 5 parts by weight, or about 0.05 to 1 part by weight based on 100 parts by weight of the hardmask composition. Within the ranges, solubility may be improved while optical properties of the hardmask composition are not changed.

According to another embodiment, an organic film produced using the hardmask composition is provided. The organic film may be, for example, formed by coating the hardmask composition on a substrate and heat-treating it for curing and may include, for example, a hardmask layer, a planarization layer, a sacrificial layer, a filler, and the like for an electronic device.

According to another embodiment, a hardmask layer including a cured product of the aforementioned hardmask composition is provided.

For example, the cured product includes a condensed polycyclic aromatic hydrocarbon.

For example, the condensed polycyclic aromatic hydrocarbon may be a substituted or unsubstituted naphthalene, a substituted or unsubstituted anthracene, a substituted or unsubstituted phenanthrene, a substituted or unsubstituted naphthacene, a substituted or unsubstituted pyrene, a substituted or unsubstituted benzopyrene, a substituted or unsubstituted chrysene, a substituted or unsubstituted triphenylene, a substituted or unsubstituted perylene, a substituted or unsubstituted benzofluoranthene, a substituted or unsubstituted benzoperylene, a substituted or unsubstituted coronene, a combination thereof, or a combined fused ring of the foregoing groups, but is not limited thereto.

As an example, the cured product may further include a heterocycle.

For example, the cured product may further include a heterocycle including at least one nitrogen atom.

For example, the cured product may further include a heterocycle including one nitrogen atom, a heterocycle including two nitrogen atoms, and a heterocycle including three nitrogen atoms.

Since the cured product includes the condensed polycyclic aromatic hydrocarbon, it may exhibit high etch resistance and chemical resistance to withstand etching gases and chemical liquids exposed in subsequent processes including etching processes.

Hereinafter, a pattern forming method using the aforementioned hardmask composition is described.

A pattern forming method according to an embodiment includes forming a material layer on a substrate, applying a hardmask composition including the aforementioned compound and solvent on the material layer, heat-treating the hardmask composition to form a hardmask layer, forming a photoresist layer on the hardmask layer, exposing and developing the photoresist layer to form a photoresist pattern, selectively removing the hardmask layer using the photoresist pattern to expose a portion of the material layer, and etching the exposed portion of the material layer.

The substrate may be for example a silicon wafer, a glass substrate, or a polymer substrate.

The material layer is a material to be finally patterned, for example a metal layer such as an aluminum layer and a copper layer, a semiconductor layer such as a silicon layer, or an insulation layer such as a silicon oxide layer and a silicon nitride layer. The material layer may be formed through a method such as a chemical vapor deposition (CVD) process.

The hardmask composition is the same as described above, and may be applied by spin-on coating in a form of a solution. Herein, a thickness of the hardmask composition is not particularly limited, but may be for example about 50 Å to 200,000 Å.

The heat-treating of the hardmask composition may be performed for example at about 100 to 700° C. for about 10 seconds to 1 hour.

For example, the method may further include forming a silicon-containing thin layer on the hardmask layer. The silicon-containing thin layer may be formed of a material, for example SiCN, SiOC, SiON, SiOCN, SiC, SiO, and/or SiN, and the like.

For example, the method may further include forming a bottom antireflective coating (BARC) on the upper surface of the silicon-containing thin layer or on the upper surface hardmask layer before forming the photoresist layer.

Exposure of the photoresist layer may be performed using, for example ArF, KrF, or EUV. After exposure, heat-treating may be performed at about 100 to 700° C.

The etching process of the exposed portion of the material layer may be performed through a dry etching process using an etching gas and the etching gas may be, for example $CHF_3$, $CF_4$, $Cl_2$, $BCl_3$, and a mixed gas thereof.

The etched material layer may be formed in a plurality of patterns, and the plurality of patterns may be a metal pattern, a semiconductor pattern, an insulation pattern, and the like, for example diverse patterns of a semiconductor integrated circuit device.

DETAILED DESCRIPTION OF THE EMBODIMENTS

Hereinafter, the embodiments are illustrated in more detail with reference to examples. However, these examples are exemplary, and the present scope is not limited thereto.

Preparation of Hardmask Composition

Example 1

After placing a stirrer in a 60 mL vial, 1,3,5-triethynylbenzene (150 mg), 2,4,5-triphenyl-3-(4-pyridylethynyl)phenylcyclopentadienone (1.46 g), and propylene glycolmonomethyl ether acetate (PGMEA, 4 mL) were placed therein and then, reacted, while stirred at 150° C. for 3 hour, synthesizing a compound represented by Chemical Formula 1a. Subsequently, the mixture was cooled to room temperature, and PGMEA (5 ml) was added thereto and then, filtered with a TEFLON (tetrafluoroethylene) filter (a pore size: 0.1 μm), preparing a hardmask composition. (MW: 1,526 g/mol)

[Chemical Formula 1a]

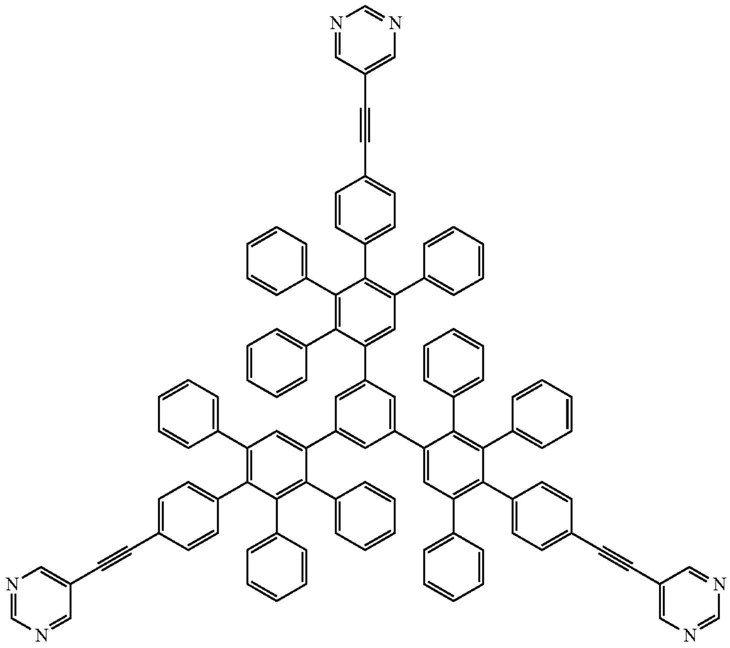

Example 2

After placing a stirrer in a 60 mL vial, 1,3,5-triethynylbenzene (150 mg), 2,5-diphenyl-3-(4-pyridylethynyl)phenyl-4-biphenylcyclopentadienone (1.69 g), and PGMEA (5 mL) were placed therein and then, reacted, while stirred at 150° C. for 3 hours, synthesizing a compound represented by Chemical Formula 2a. Subsequently, this mixture was cooled to room temperature, PGMEA (7 ml) was further added thereto and then, filtered with a TEFLON (tetrafluoroethylene) filter (a pore size: 0.1 μm), preparing a hardmask composition. (MW: 1,754 g/mol)

[Chemical Formula 2a]

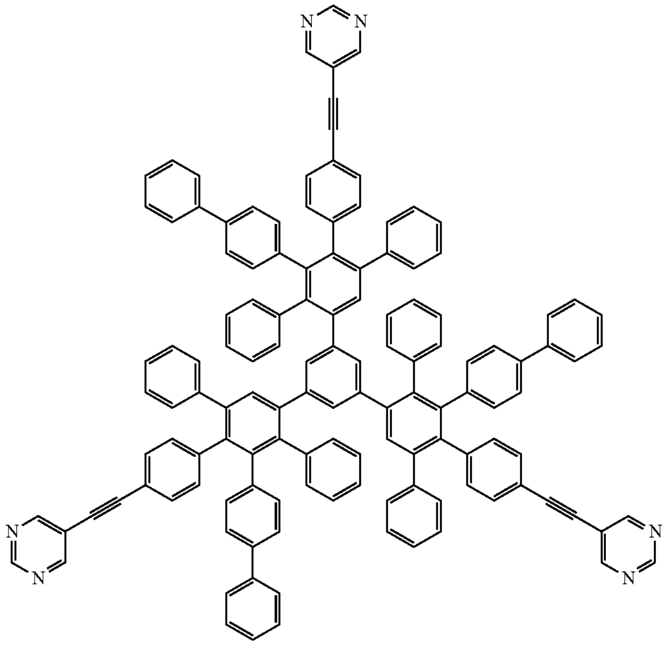

Example 3

After placing a stirrer in a 60 mL vial, 1,3,5-triethynylbenzene (150 mg), 2,4,5-triphenyl-3-(4-methoxynaphthylethynyl)phenylcyclopentadienone (1.69 g), and PGMEA (5 mL) were placed therein and then, reacted, while stirred at 150° C. for 3 hours, synthesizing a compound represented by Chemical Formula 3a. Subsequently, the mixture was cooled to room temperature, and PGMEA (7 ml) was further added thereto and then, filtered with a TEFLON (tetrafluoroethylene) filter (a pore size: 0.1 μm), preparing a hardmask composition. (MW: 1,760 g/mol)

[Chemical Formula 3a]

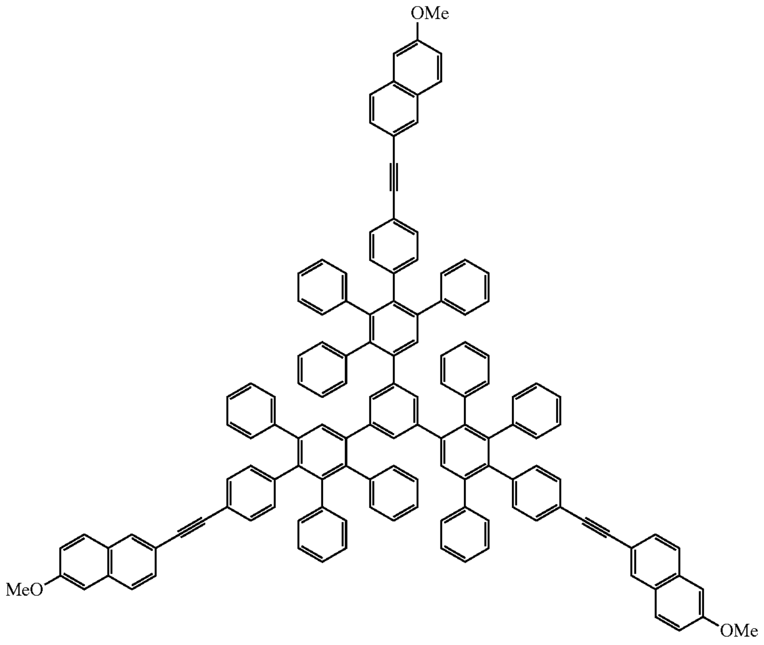

Example 4

After placing a stirrer in a 60 mL vial, the compound (1.53 g) represented by Chemical Formula 1a obtained by drying the mixture of Example 1, 2,4,5-triphenyl-3-[2-(6-methoxy)naphthyl]cyclopentadienone (1.39 g) and PGMEA (8 mL) were added thereto and then, reacted, while stirred at 250° C. for 3 hour, synthesizing a compound represented by Chemical Formula 4a. Subsequently, the mixture was cooled to room temperature, and 11 ml of PGMEA was further added thereto and then, filtered with a TEFLON (tetrafluoroethylene) filter (a pore size: 0.1 μm), preparing a hardmask composition. (MW: 2,836 g/mol)

[Chemical Formula 4a]

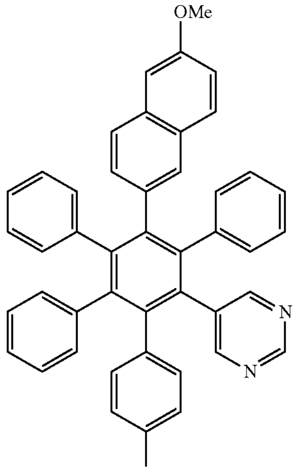

-continued

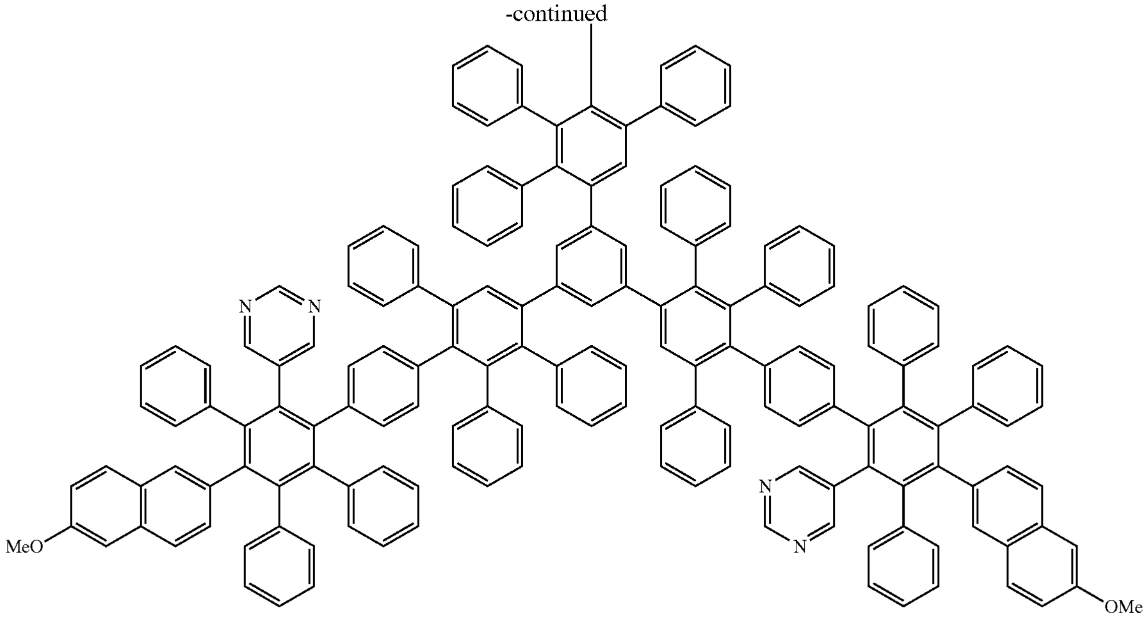

Example 5

After placing a stirrer in a 60 mL vial, the compound (1.75 g) represented by Chemical Formula 2a obtained by drying the mixture of Example 2, 2,5-diphenyl-3,4-di[2-(6-methoxy)naphthyl]cyclopentadienone (1.63 g), and PGMEA (9 mL) were placed therein and then, reacted, while stirred at 250° C. for 3 hours, synthesizing a compound represented by Chemical Formula 5a. Subsequently, the mixture was cooled to room temperature, and 12 ml of PGMEA was further added thereto and then, filtered with a TEFLON (tetrafluoroethylene) filter (a pore size: 0.1 μm), preparing a hardmask composition. (MW: 3,076 g/mol)

[Chemical Formula 4a]

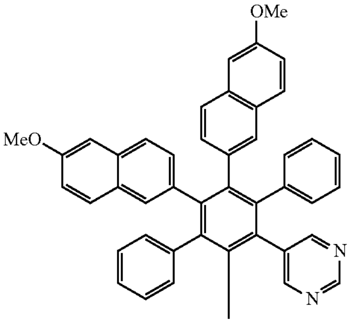

-continued

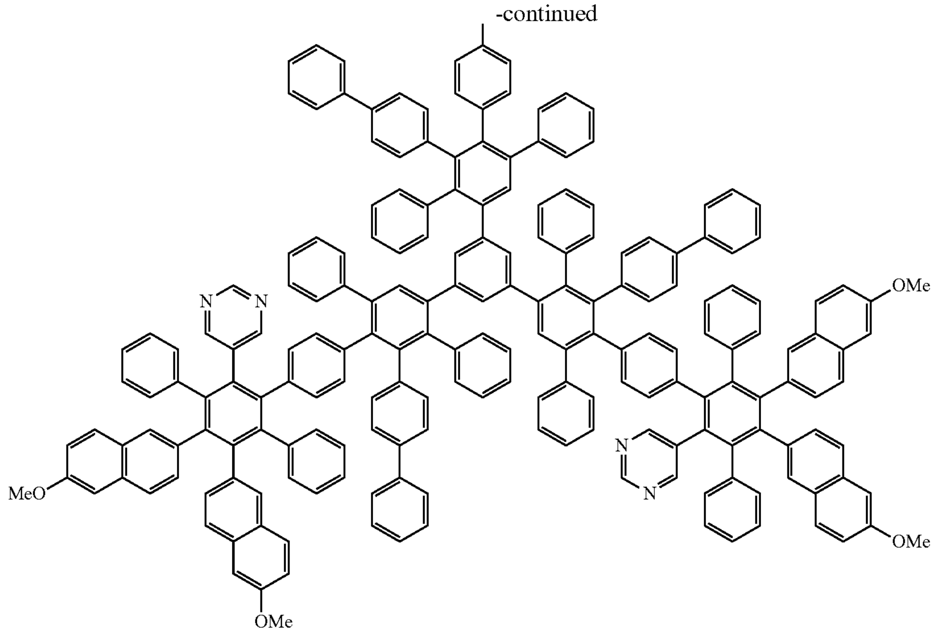

Example 6

After placing a stirrer in a 60 mL vial, 3,3',5'5'-tetraethynylbiphenyl (250 mg), 2,5-diphenyl-3-(4-pyridylethynyl)phenyl-4-biphenylcyclopentadienone (2.25 g), and PGMEA (7 mL) were placed therein and then, reacted, while stirred at 150° C. for 3 hours, synthesizing a compound represented by Chemical Formula 6a. Subsequently, the mixture was cooled to room temperature, and PGMEA (9 ml) was further added thereto and then, filtered with a TEFLON (tetrafluoroethylene) filter (a pore size: 0.1 μm), preparing a hardmask composition. (MW: 2,389 g/mol)

Example 7

After placing a stirrer in a 60 mL vial, 3,3',5'5'-tetraethynylbiphenyl (250 mg), 2,4,5-triphenyl-3-(4-methoxynaphthylethynyl)phenylcyclopentadienone (2.26 g), and PGMEA (7 mL) were placed therein and then, reacted, while stirred at 150° C. for 3 hours, synthesizing a compound represented by Chemical Formula 7a. Subsequently, the mixture was cooled to room temperature, and PGMEA (9 ml) was further added thereto and then, filtered with a TEFLON (tetrafluoroethylene) filter (a pore size: 0.1 μm), preparing a hardmask composition. (MW: 2,397 g/mol)

[Chemical Formula 6a]

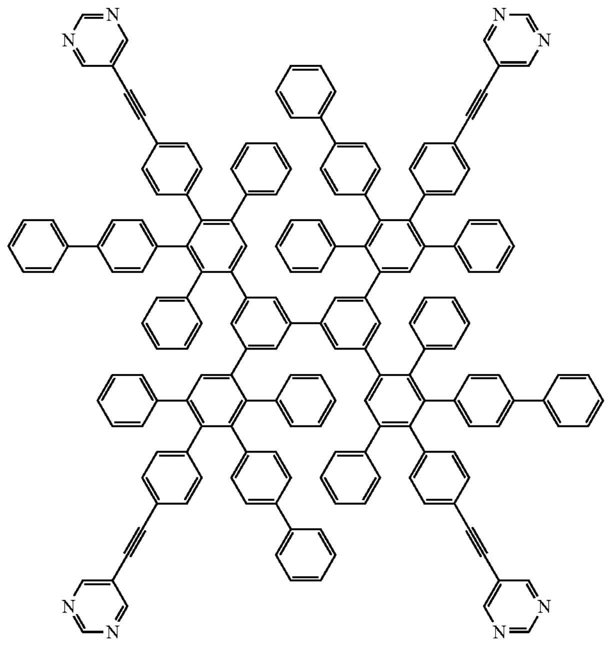

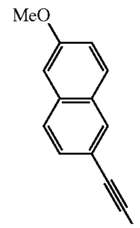

[Chemical Formula 7a]

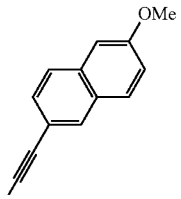

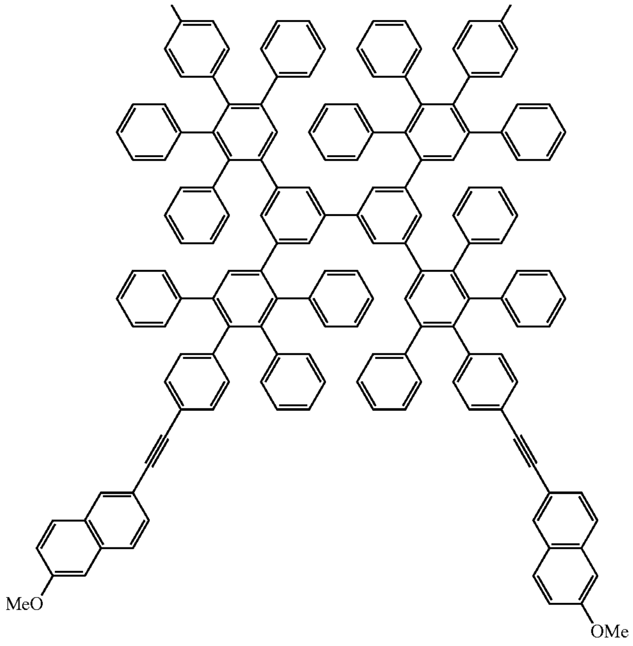

Example 8

After placing a stirrer in a 60 mL vial, the compound (2.39 g) represented by Chemical Formula 6a obtained by drying the mixture of Example 6, 2,5-diphenyl-3,4-di[2-(6-methoxy)naphthyl]cyclopentadienone (2.18 g), and PGMEA (13 mL) were placed therein and then, reacted, while stirred at 250° C. for 3 hours, synthesizing a compound represented by Chemical Formula 8a. Subsequently, the mixture was cooled to room temperature, and PGMEA (17 ml) was further added thereto and then, filtered with a TEFLON (tetrafluoroethylene) filter (a pore size: 0.1 μm), preparing a hardmask composition. (MW: 4,456 g/mol)

[Chemical Formula 8a]

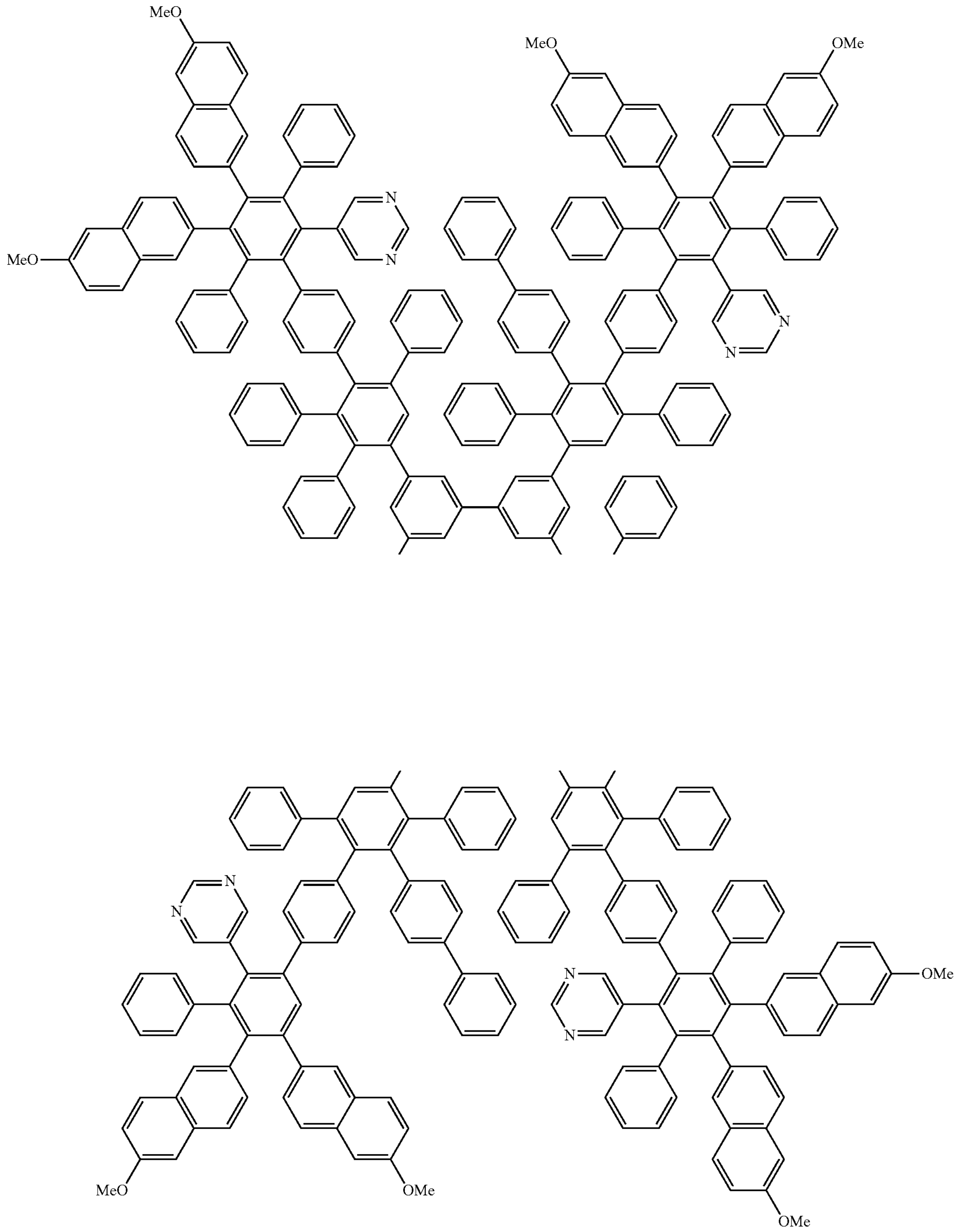

Example 9

After placing a stirrer in a 60 mL vial, the compound (2.40 g) represented by Chemical Formula 7a obtained by drying the mixture of Example 7, 2,5-diphenyl-3,4-di[2-(6-methoxy)naphthyl]cyclopentadienone (2.18 g), and PGMEA (13 mL) were placed therein and then, reacted, while stirred at 250° C. for 3 hours, synthesizing a compound represented by Chemical Formula 9a. Subsequently, the mixture was cooled to room temperature, and PGMEA (17 ml) was further added thereto and then, filtered with a TEFLON (tetrafluoroethylene) filter (a pore size: 0.1 μm), preparing a hardmask composition. (MW: 4,464 g/mol)

[Chemical Formula 9a]

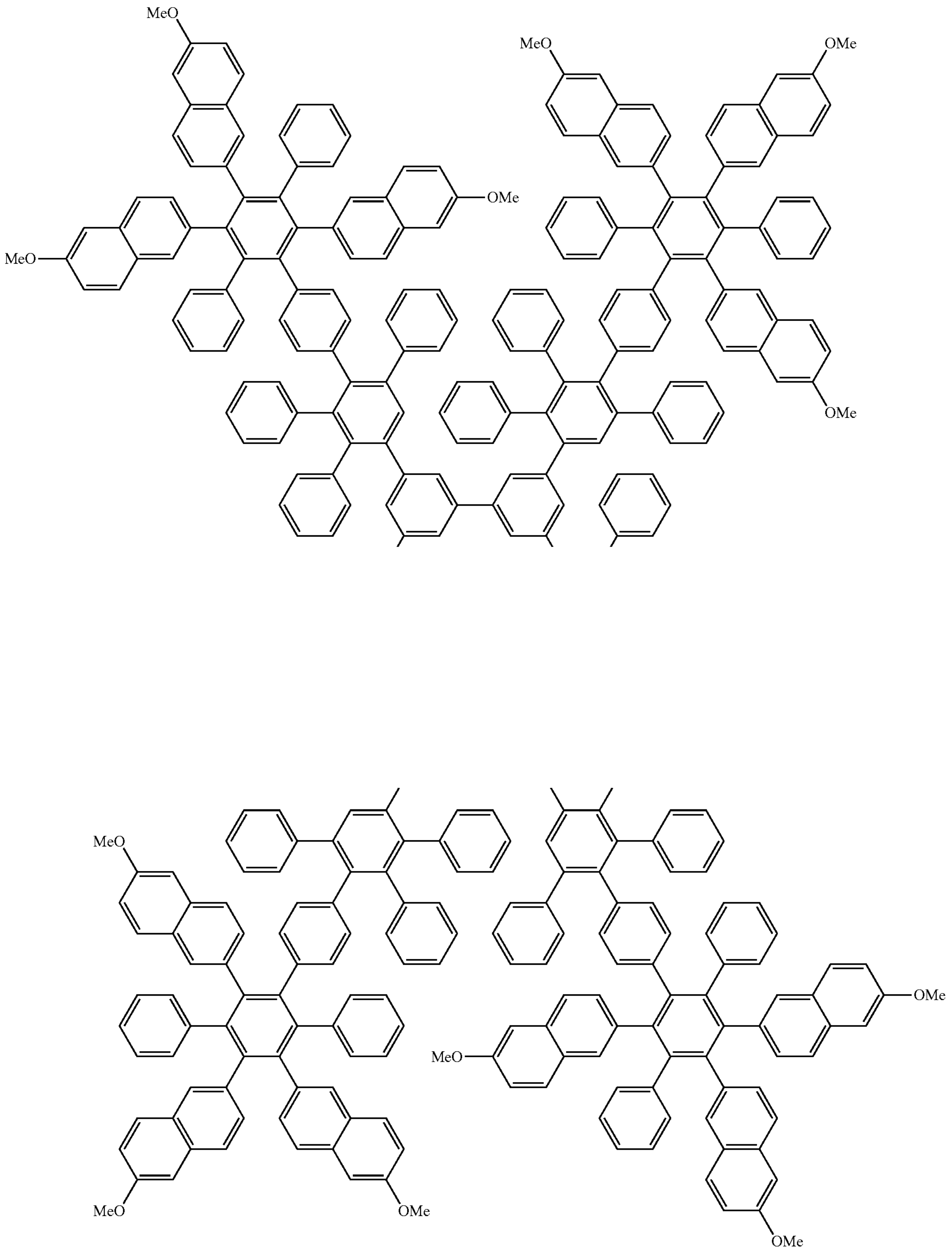

Comparative Example 1

After placing a stirrer in a 60 mL vial, 1,3,5-triethynylbenzene (150 mg), 2,4,5-triphenyl-3-(4-phenylethynyl)phenylcyclopentadienone (1.45 g), and PGMEA (4 mL) were placed therein and then, reacted, while stirred at 150° C. for 3 hours, synthesizing a compound represented by Chemical Formula A. Subsequently, the mixture was cooled to room temperature, and PGMEA (5 ml) was further added thereto and then, filtered with a TEFLON (tetrafluoroethylene) filter (a pore size: 0.45 μm), preparing a hardmask composition. (MW: 1,520 g/mol)

[Chemical Formula A]

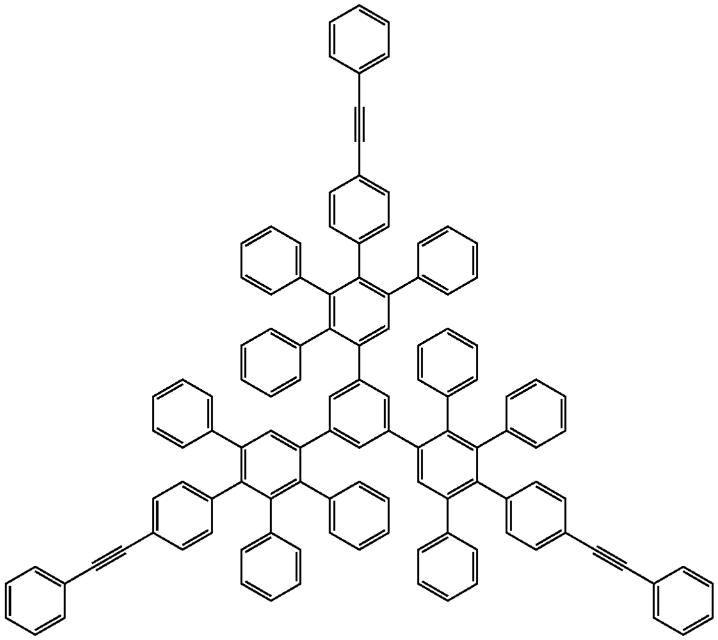

Comparative Example 2

After placing a stirrer in a 60 mL vial, 3,3',5,5'-tetraethynylbiphenyl (250 mg), 2,4,5-triphenyl-3-(4-phenylethynyl)phenylcyclopentadienone (1.94 g), and PGMEA (6 mL) were placed therein and then, reacted, while stirred at 150° C. for 3 hours, synthesizing a compound represented by Chemical Formula B. Subsequently, the mixture was cooled to room temperature, and PGMEA (8 ml) was further added thereto and then, filtered with a TEFLON (tetrafluoroethylene) filter (a pore size: 0.45 μm), preparing a hardmask composition. (MW: 2,077 g/mol)

[Chemical Formula B]

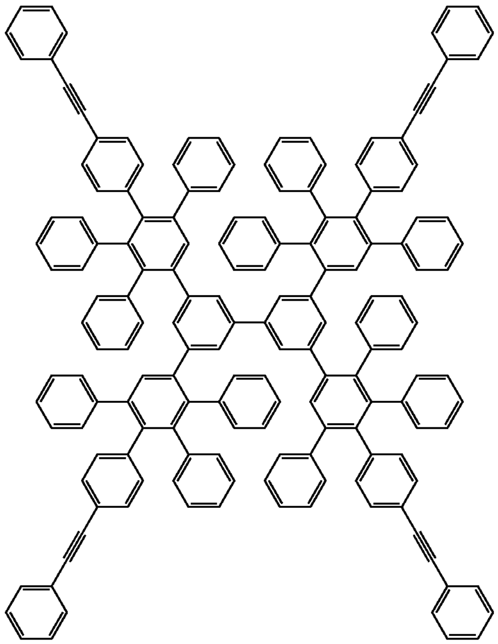

Comparative Example 3

After placing a stirrer in a 60 mL vial, the compound (1.52 g) represented by Chemical Formula A obtained by drying the mixture of Comparative Example 1, tetraphenylcyclopentadienone (1.15 g), and PGMEA (7 mL) were placed therein and then, reacted, while stirred at 250° C. for 3 hours, synthesizing a compound represented by Chemical Formula C. Subsequently, the mixture was cooled to room temperature, and PGMEA (8 ml) was further added thereto and then, filtered with a TEFLON (tetrafluoroethylene) filter (a pore size: 2.7 μm), preparing a hardmask composition. (MW: 2,589 g/mol)

[Chemical Formula C]

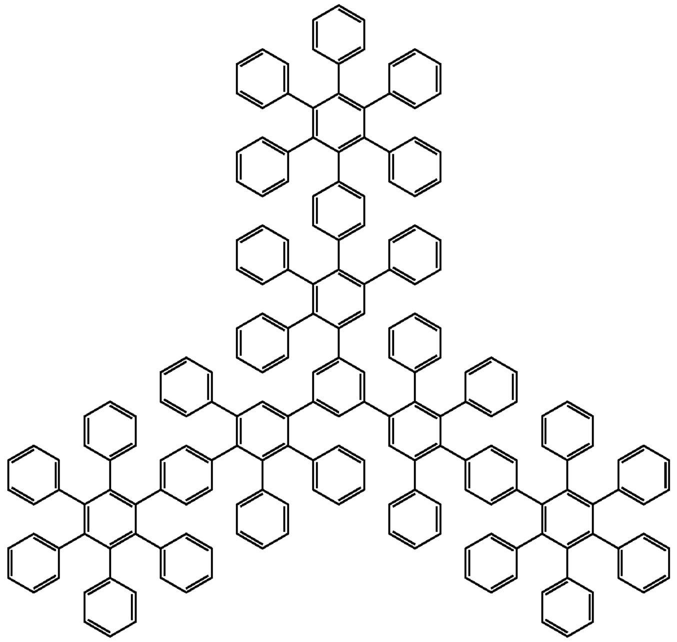

Comparative Example 4

After placing a stirrer in a 60 mL vial, the compound (2.08 g) represented by Chemical Formula B obtained by drying the mixture of Comparative Example 2, tetraphenylcyclopentadienone (1.54 g), and PGMEA (9 mL) were placed therein and then, reacted, while stirred at 250° C. for 3 hours, synthesizing a compound represented by Chemical Formula D. Subsequently, the mixture was cooled to room temperature, and PGMEA (12 ml) was further added thereto and then, filtered with a TEFLON (tetrafluoroethylene) filter (a pore size: 2.7 μm), preparing a hardmask composition. (MW: 3,503 g/mol)

[Chemical Formula D]

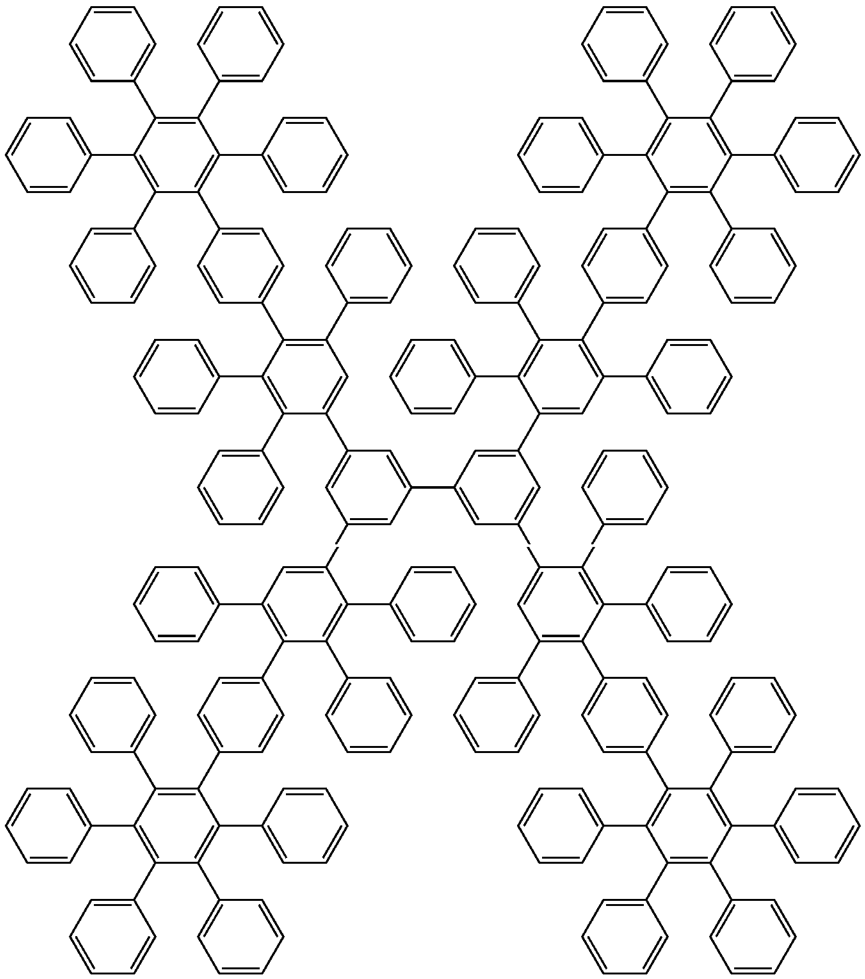

Formation of Organic Film

The hardmask compositions according to Examples 1 to 9 and Comparative Examples 1 to 4 were respectively spin-coated on the following silicon wafer, cured under a nitrogen atmosphere for 30 minutes with a UV curing machine, and heat-treated under a nitrogen atmosphere at 550° C. for 2 minutes, forming each 4,000 Å to 6,000 Å-thick organic film.

Evaluation: Etch Resistance

Whether the organic films formed of the hardmask compositions according to Examples 1 to 9 and Comparative Examples 1 to 4 were delaminated or not was examined, and then, a thickness of the organic films was measured. Subsequently, the organic films were dry-etched by using $CF_x$ mixed gas for 100 seconds, and then, a thickness thereof after the dry etching was measured.

A thickness difference of each organic film before and after the dry etching and etching time were used to calculate a bulk etch rate (BER) according to Calculation Equation 1.

Etch rate (Å/s)=(initial thickness of organic film−thickness of the organic film after etching)/etching time [Calculation Equation 1]

The results are shown in Table 1.

TABLE 1

| | Delamination | $CF_x$ Bulk etch rate (Å/s) |
|---|---|---|
| Example 1 | No delamination | 22.8 |
| Example 2 | No delamination | 22.7 |
| Example 3 | No delamination | 23.5 |
| Example 4 | No delamination | 22.9 |
| Example 5 | No delamination | 23.4 |
| Example 6 | No delamination | 22.6 |
| Example 7 | No delamination | 23.3 |
| Example 8 | No delamination | 23.1 |
| Example 9 | No delamination | 23.5 |
| Comparative Example 1 | Delaminated | unmeasurable |
| Comparative Example 2 | Delaminated | unmeasurable |
| Comparative Example 3 | Delaminated | unmeasurable |
| Comparative Example 4 | Delaminated | unmeasurable |

Referring to Table 1, the organic films according to Comparative Examples 1 to 4 were delaminated and not uniform and thus not suitable for being applied as a hard mask, and accordingly, it was impossible to measure a thickness thereof and thus difficult to evaluate etch resistance.

On the other hand, the organic films according to Examples 1 to 9 were not delaminated but uniform and thus exhibited sufficient etch resistance to etching gas.

While this invention has been described in connection with what is presently considered to be practical example embodiments, it is to be understood that the invention is not limited to the disclosed embodiments. On the contrary, it is intended to cover various modifications and equivalent arrangements included within the spirit and scope of the appended claims.

What is claimed is:

1. A pattern forming method, the method comprising:

applying a hardmask composition comprising a compound represented by Chemical Formula 1 and a solvent on a material layer and heat-treating the resultant to form a hardmask layer, forming a photoresist layer on the hardmask layer, exposing and developing the photoresist layer to form a photoresist pattern, selectively removing the hardmask layer using the photoresist pattern to expose a portion of the material layer, and etching an exposed part of the material layer:

[Chemical Formula 1]

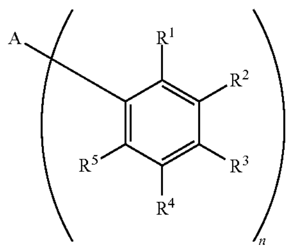

wherein, in Chemical Formula 1,

A is a C6 to C30 aromatic moiety, $R^1$ to $R^5$ are each independently hydrogen, a substituted or unsubstituted C6 to C30 aryl group, a substituted or unsubstituted C3 to C30 heteroaryl group, or a combination thereof or a group represented by Chemical Formula 2, at least one of $R^1$ to $R^5$ is a group represented by Chemical Formula 2, at least one of $R^1$ to $R^5$ not represented by Chemical Formula 2 is a substituted or unsubstituted C6 to C30 aryl group, a substituted or unsubstituted C3 to C30 heteroaryl group, or a combination thereof, and n is an integer greater than or equal to 2,

[Chemical Formula 2]

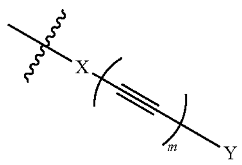

wherein, in Chemical Formula 2,

X is a substituted or unsubstituted C6 to C30 arylene group,

Y is a substituted C6 to C60 aryl group or a substituted or unsubstituted C3 to C60 heteroaryl group, wherein the substituted C6 to C60 aryl group includes a substituent selected from a substituted or unsubstituted C1 to C30 alkoxy group, a substituted or unsubstituted C1 to C30 alkylthiol group, a substituted or unsubstituted C1 to C20 alkylamine group, a substituted or unsubstituted C3 to C30 heteroaryl group, or a combination thereof, m is 0 or 1, and

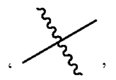, indicates a linking point with Chemical Formula 1, and wherein when A is a C6 aromatic moiety and Y is a substituted C6 to C60 aryl group, Y includes a substituent selected from a substituted or unsubstituted C1 to C30 alkylthiol group, a substituted or unsubstituted C1 to C20 alkylamine group, a substituted or unsubstituted C3 to C30 heteroaryl group that is not a pyridine group, or a combination thereof.

2. The pattern forming method of claim 1, wherein A is a benzene moiety, a naphthalene moiety, an anthracene moiety, a tetracene moiety, a pentacene moiety, a biphenyl moiety, a terphenyl moiety, a quaterphenyl moiety, or a quinquephenyl moiety, a phenanthrene moiety, a pyrene moiety, a fluoranthene moiety, a benzophenanthrene moiety, a chrysene moiety, a perylene moiety, a benzopyrene moiety, a picene moiety, a benzofluoranthene moiety, a dibenzofluoranthene moiety, a benzoperylene moiety, a coronene moiety, a naphthoanthracene moiety, or a triphenylene moiety.

3. The pattern forming method of claim 1, wherein A is a moiety of Group 1:

[Group 1]

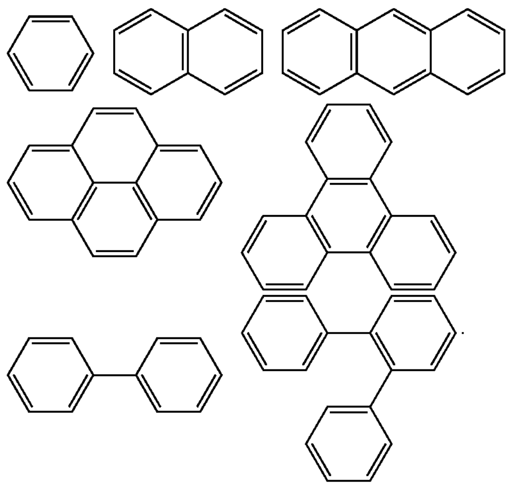

4. The pattern forming method of claim 1, wherein:

$R^1$, $R^2$, $R^4$, and $R^5$ are each independently hydrogen or a substituted or unsubstituted group selected from Group 2, and $R^3$ is the group represented by Chemical Formula 2:

[Group 2]

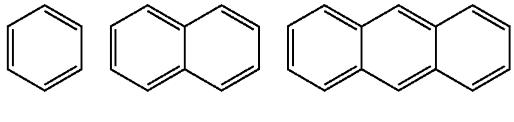

-continued

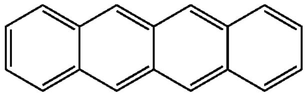

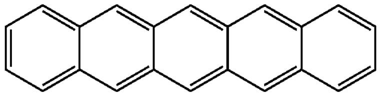

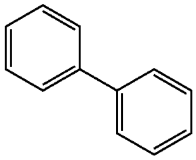

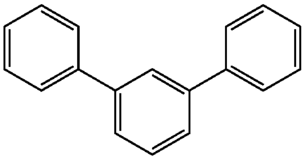

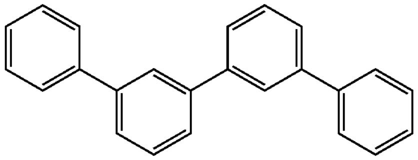

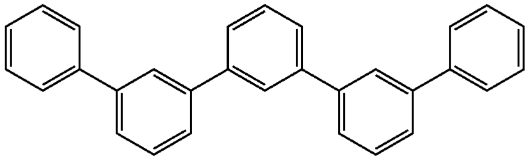

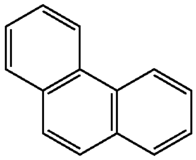

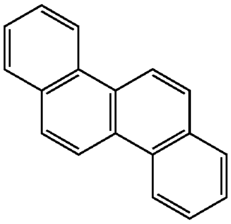

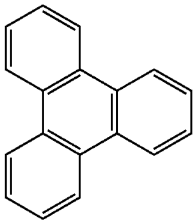

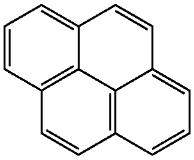

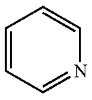

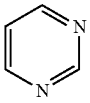

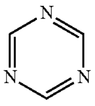

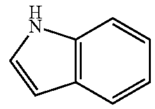

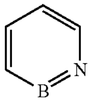

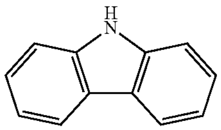 [SMILES: c1ccc2c(c1)[nH]c1ccccc12]

.

5. The pattern forming method of claim 1, wherein:

$R^1$ and $R^4$ are each independently a substituted or unsubstituted phenyl group, and $R^5$ is hydrogen.

6. The pattern forming method of claim 1, wherein:

X is any one of substituted or unsubstituted selected groups from Group 3:

[Group 3]

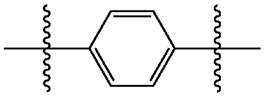

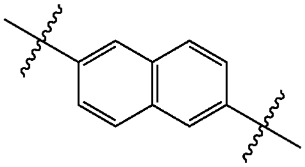

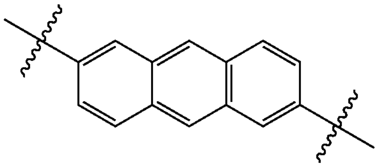

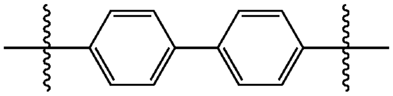

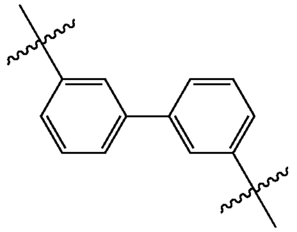

wherein, in Group 3,

, means a linking point.

7. The pattern forming method of claim 1, wherein:

the group represented by Chemical Formula 2 is represented by Chemical Formula 3 or 4:

[Chemical Formula 3]

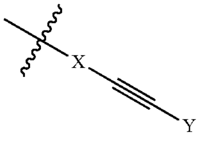

[Chemical Formula 4]

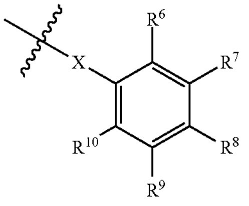

wherein, in Chemical Formula 3 and Chemical Formula 4,

X is a substituted or unsubstituted C6 to C30 arylene group,

Y is a substituted or unsubstituted C3 to C30 heteroaryl group; or a C6 to C30 aryl group substituted with a substituted or unsubstituted C1 to C30 alkoxy group, a substituted or unsubstituted C1 to C30 alkylthiol group, a substituted or unsubstituted C1 to C20 alkylamine group, or a combination thereof, $R^6$ to $R^{10}$ are each independently hydrogen, a substituted or unsubstituted C6 to C30 aryl group, a substituted or unsubstituted C3 to C30 heteroaryl group, or a combination thereof, at least one of $R^6$ to $R^{10}$ is a substituted or unsubstituted C3 to C30 nitrogen-containing heteroaryl group; or a C6 to C30 aryl group substituted with a substituted or unsubstituted C1 to C30 alkoxy group, a substituted or unsubstituted C1 to C30 alkylthiol group, a substituted or unsubstituted C1 to C20 alkylamine group, or a combination thereof, and

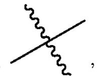, indicates a linking point with Chemical Formula 1, and wherein when A of Chemical Formula 1 is a C6 aromatic moiety and Y of Chemical Formula 3 is a substituted C6 to C60 aryl group, Y includes a substituent selected from a substituted or unsubstituted C1 to C30 alkylthiol group, a substituted or unsubstituted C1 to C20 alkylamine group, a substituted or unsubstituted C3 to C30 heteroaryl group that is not a pyridine group, or a combination thereof, and wherein when A of Chemical Formula 1 is a C6 aromatic moiety, at least one of $R^6$ to $R^{10}$ of Chemical Formula 4 is a substituted or unsubstituted C3 to C30 nitrogen-containing heteroaryl group that is not a pyridine group; or a C6 to C30 aryl group substituted with a substituted or unsubstituted C1 to C30 alkylthiol group, a substituted or unsubstituted C1 to C20 alkylamine group, or a combination thereof.

8. The pattern forming method of claim 7, wherein:

the group represented by Chemical Formula 2 is represented by Chemical Formula 3, and Y of Chemical Formula 3 is a substituted or unsubstituted C3 to C30 nitrogen-containing heteroaryl group selected from Group 4; or a C6 to C30 aryl group substituted with a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 5:

[Group 4]

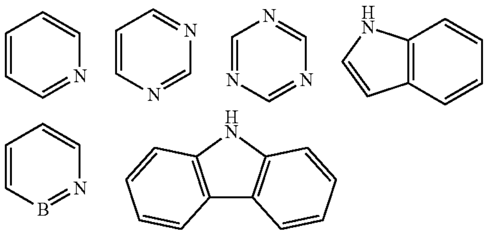

[Group 5]

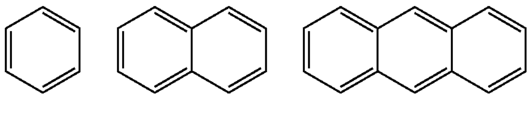

-continued

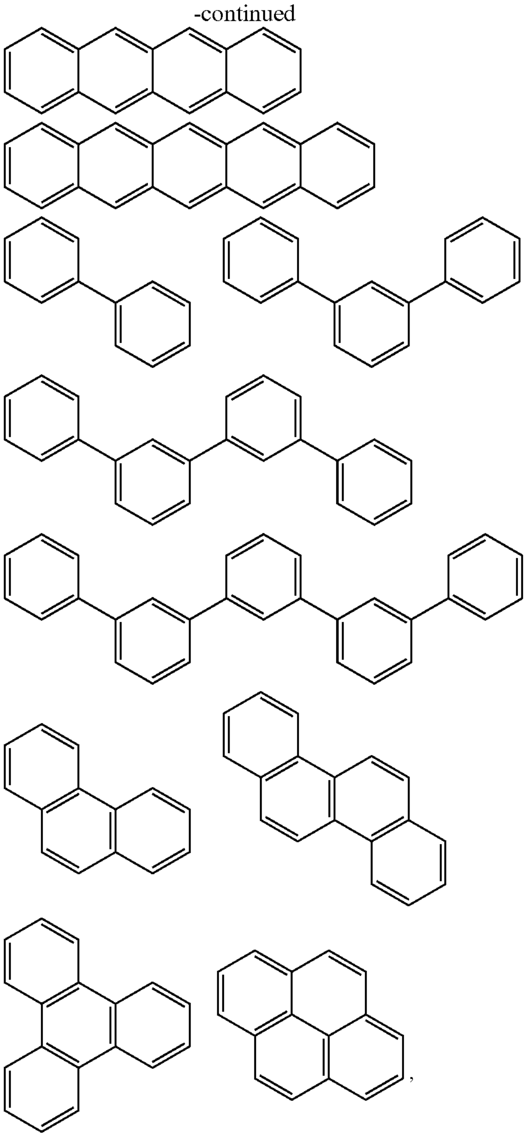, and provided that when A of Chemical Formula 1 is a C6 aromatic moiety and Y of Chemical Formula 3 is a substituted C6 to C60 aryl group, Y of Chemical Formula 3 includes a substituent selected from a substituted or unsubstituted C1 to C30 alkylthiol group, a substituted or unsubstituted C1 to C20 alkylamine group, a substituted or unsubstituted C3 to C30 heteroaryl group that is not a pyridine group, or a combination thereof.

9. The pattern forming method of claim 7, wherein:

the group represented by Chemical Formula 2 is represented by Chemical Formula 4, $R^6$ to $R^{10}$ of Chemical Formula 4 are each independently a substituted or unsubstituted C3 to C30 nitrogen-containing heteroaryl group selected from Group 6 or a substituted or unsubstituted C6 to C30 aryl group selected from Group 7, and at least one of $R^7$, $R^8$, and $R^{10}$ is a substituted or unsubstituted C3 to C30 nitrogen-containing heteroaryl group selected from Group 6; or a C6 to C30 aryl group substituted with a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7:

[Group 6]

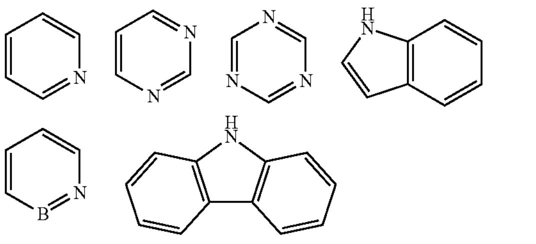

[Group 7]

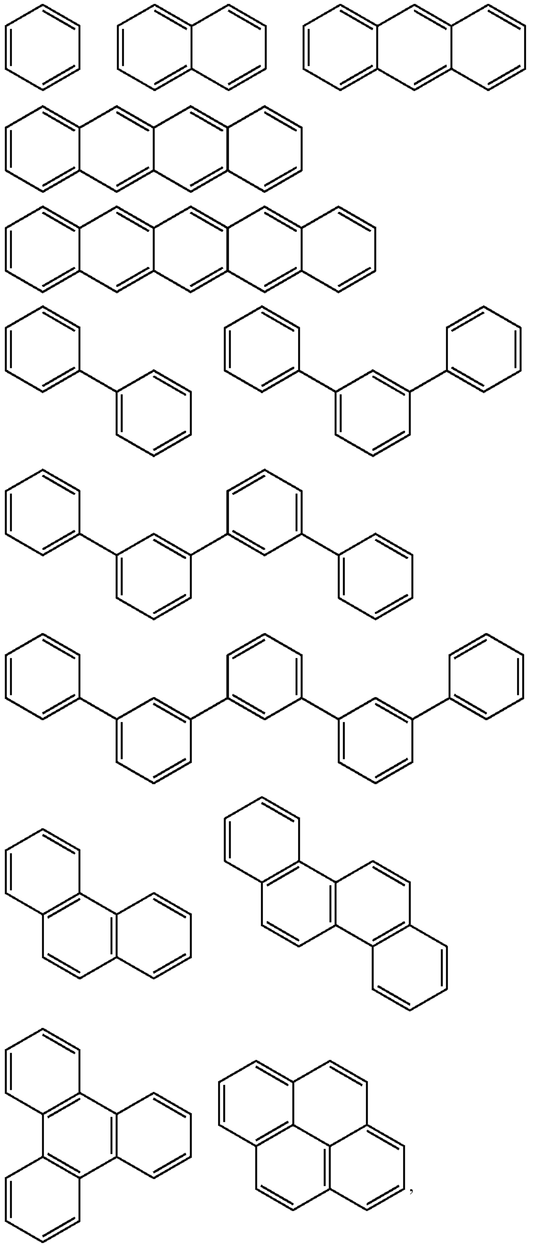

, and provided that when A of Chemical Formula 1 is a C6 aromatic moiety, at least one of $R^6$ to $R^{10}$ of Chemical Formula 4 is a substituted or unsubstituted C3 to C30 nitrogen-containing heteroaryl group that is not a pyridine group; or a C6 to C30 aryl group substituted a substituted or unsubstituted C1 to C30 alkylthiol group, a substituted or unsubstituted C1 to C20 alkylamine group, or a combination thereof.

10. The pattern forming method of claim 9, wherein $R^6$ and $R^9$ are each independently a substituted or unsubstituted phenyl group.

11. The pattern forming method of claim 9, wherein:

$R^8$ is a C6 to C30 aryl group substituted a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7, and $R^{10}$ is a substituted or unsubstituted C3 to C30 nitrogen-containing heteroaryl group selected from Group 6; or a C6 to C30 aryl group substituted with a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7.

12. The pattern forming method of claim 1, wherein:

n is an integer satisfying the range of $2 \leq n \leq k/2$, and k is a number of substitutable positions of A in Chemical Formula 1.

13. The pattern forming method of claim 1, wherein a molecular weight of the compound represented by Chemical Formula 1 is 900 g/mol to 7,000 g/mol.

14. The pattern forming method of claim 1, wherein the compound represented by Chemical Formula 1 is included in an amount of 0.01 wt % to 30 wt % based on the total content of the hard mask composition.

15. The pattern forming method of claim 1, wherein Y of Chemical Formula 2 is a substituted C6 to C60 aryl group or a substituted or unsubstituted C3 to C60 heteroaryl group, wherein the substituted C6 to C60 aryl group includes a substituent selected from a substituted or unsubstituted C1 to C20 alkylamine group, a substituted or unsubstituted C3 to C30 heteroaryl group, or a combination thereof.

16. A pattern forming method, the method comprising:

applying a hardmask composition comprising a compound represented by Chemical Formula 1 and a solvent on a material layer and heat-treating the resultant to form a hardmask layer, forming a photoresist layer on the hardmask layer, exposing and developing the photoresist layer to form a photoresist pattern, selectively removing the hardmask layer using the photoresist pattern to expose a portion of the material layer, and etching an exposed part of the material layer:

[Chemical Formula 1]

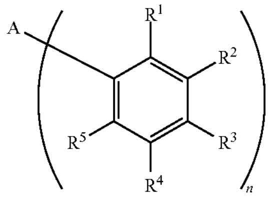

wherein, in Chemical Formula 1,

A is a C6 to C30 aromatic moiety, $R^1$ to $R^5$ are each independently hydrogen, a substituted or unsubstituted C6 to C30 aryl group, a substituted or unsubstituted C3 to C30 heteroaryl group, or a combination thereof or a group represented by Chemical Formula 4, at least one of $R^1$ to $R^5$ is a group represented by Chemical Formula 4, at least one of $R^1$ to $R^5$ not represented by Chemical Formula 4 is a substituted or unsubstituted C6 to C30 aryl group, a substituted or unsubstituted C3 to C30 heteroaryl group, or a combination thereof, and n is an integer greater than or equal to 2,

[Chemical Formula 4]

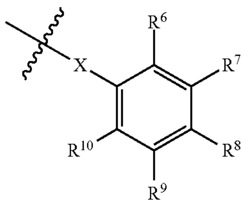

wherein, in Chemical Formula 4,

X is a substituted or unsubstituted C6 to C30 arylene group, $R^6$ to $R^{10}$ of Chemical Formula 4 are each independently a substituted or unsubstituted C3 to C30 nitrogen-containing heteroaryl group selected from Group 6 or a substituted or unsubstituted C6 to C30 aryl group selected from Group 7, and at least one of $R^7$, $R^8$, and $R^{10}$ is a substituted or unsubstituted C3 to C30 nitrogen-containing heteroaryl group selected from Group 6; or a C6 to C30 aryl group substituted with a substituted or unsubstituted C1 to C30 alkoxy group, a substituted or unsubstituted C1 to C30 alkylthiol group, a substituted or unsubstituted C1 to C20 alkylamine group, or a combination thereof which is selected from Group 7:

[Group 6]

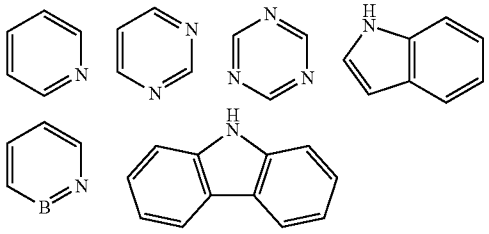

[Group 7]

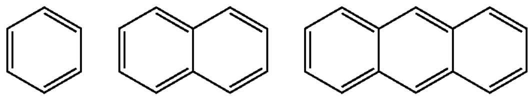

-continued

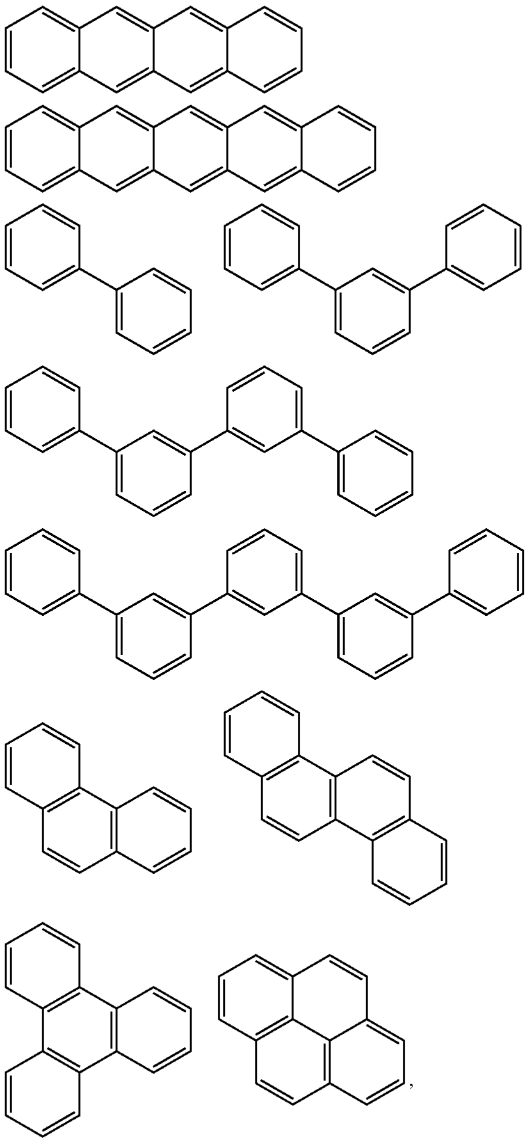

,

'' indicates a linking point with Chemical Formula 1, and provided that when A of Chemical Formula 1 is a C6 aromatic moiety, at least one of $R^6$ to $R^{10}$ of Chemical Formula 4 is a substituted or unsubstituted C3 to C30 nitrogen-containing heteroaryl group that is not a pyridine group; or a C6 to C30 aryl group substituted with a hydroxy group, an amine group, a mercapto group, a substituted or unsubstituted C1 to C30 alkylthiol group, a substituted or unsubstituted C1 to C20 alkylamine group, or a combination thereof.

* * * * *